US009273345B2

(12) United States Patent
Kiel et al.

(10) Patent No.: US 9,273,345 B2
(45) Date of Patent: Mar. 1, 2016

(54) METHODS AND COMPOSITIONS FOR PROCESSES OF RAPID SELECTION AND PRODUCTION OF NUCLEIC ACID APTAMERS

(75) Inventors: Johnathan L. Kiel, Brooks City-Base, TX (US); Eric A. Holwitt, Brooks City-Base, TX (US); Michael (Maomian) Fan, Brooks City-Base, TX (US); Shelly D. Roper, Brooks City-Base, TX (US)

(73) Assignee: CONCEPTUAL MINDWORKS, INC., San Antonio, TX (US)

( * ) Notice: Subject to any disclaimer, the term of this patent is extended or adjusted under 35 U.S.C. 154(b) by 1038 days.

(21) Appl. No.: 11/965,039

(22) Filed: Dec. 27, 2007

(65) Prior Publication Data
US 2009/0004644 A1   Jan. 1, 2009

Related U.S. Application Data

(60) Provisional application No. 60/882,454, filed on Dec. 28, 2006, provisional application No. 60/989,602, filed on Nov. 21, 2007.

(51) Int. Cl.
*C12N 15/115* (2010.01)
*C12Q 1/68* (2006.01)

(52) U.S. Cl.
CPC ............ *C12Q 1/6811* (2013.01); *C12N 15/115* (2013.01); *Y10T 436/143333* (2015.01)

(58) Field of Classification Search
None
See application file for complete search history.

(56) References Cited

U.S. PATENT DOCUMENTS

| 5,925,517 | A  | * | 7/1999  | Tyagi et al. ..................... 435/6.1 |
| 5,928,862 | A  | * | 7/1999  | Morrison .......................... 435/6 |
| 2002/0045272 | A1 | * | 4/2002  | McDevitt et al. ............. 436/518 |
| 2004/0009514 | A1 | * | 1/2004  | Frutos et al. ...................... 435/6 |
| 2005/0089864 | A1 | * | 4/2005  | Li et al. ............................ 435/6 |
| 2005/0272088 | A1 | * | 12/2005 | Cook et al. ........................ 435/6 |

OTHER PUBLICATIONS

Polysciences, Inc. webpage at: http://www.polysciences.com/Catalog/Department/81/categoryId__321/ [online] [retrieved on Jan. 31, 2010] (2 pages).*
Fan et al. Apatmer selection express: A novel method for rapid single-step selection and sensing of aptamers. Journal of Biomolecular Techniques 19:311-321 (2008).*
Gill et al. Fluorescence resonance energy transfer in CdSe/ZnS-DNA conjugates: probing hybridization and DNA cleavage. J. Phys. Chem. B 109:23715-9, published online Nov. 19, 2005.*
Levy et al. Quantum-dot aptamer beacons for the detection of proteins. ChemBioChem 6:2163-6, published online Oct. 27, 2005.*

(Continued)

*Primary Examiner* — Samuel Woolwine
(74) *Attorney, Agent, or Firm* — Faegre Baker Daniels LLP

(57) ABSTRACT

Embodiments herein relate to compositions and methods for making and using aptamers, for example, DNA aptamers (DCEs) and/or RNA aptamers. In some embodiments, methods relate to making and amplifying target DCEs. In certain embodiments, methods for making capture elements or aptamers concern using a reporter moiety and signal reducing moiety prior to amplifying a target-specific capture element. In some embodiments, methods disclosed herein may be used to rapidly generate large quantities of aptamers such as DCEs directed to a particular target agent. Some embodiments relate to systems for performing automated generation of aptamers.

17 Claims, 24 Drawing Sheets

(56) References Cited

OTHER PUBLICATIONS

Zhu et al. Aptamer based microsphere biosensor for thrombin detection. Sensors 6:785-95, Aug. 16, 2006.*
Frutos et al. Method for detection of single-base mismatches using bimolecular beacons. J Am Chem Soc 124(11):2396-2397 (2002).*
Dyadyusha et al. Quenching of CdSe quantum dot emission, a new approach for biosensing. Chem Commun:3201-3203 (2005).*
Konforti et al. DNA substrate requirements for stable joint molecule formation by the RecA and single-stranded DNA-binding proteins of *Escherichia coli*. The Journal of Biological Chemistry 266(16):10112-10121 (1991).*
Hamaguchi et al. Analytical Biochemistry 294:126-131 (2001).*
Butenas et al. Blood 94(7):2169-2178 (1999).*
Kim et al. (Sensor and Actuators B 102:315-319 (2004).*
Anant K. Singh, Wentong Lu, Dulal Senapati, Sadia Afrin Khan, Zhen Fan, Tapas Senapati, Teresa Demeritte, Lule Beqa, and Paresh Chandra Ray "Long Range Nanoparticle Surface Energy Transfer Ruler for Monitoring Photothermal Therapy Response" Small. Sep. 5, 2011; 7(17): 2517-2525. doi:10.1002/smll.201100591.
Eyal Shafran, Benjamin D. Mangum,† and Jordan M. Gerton; "Energy Transfer from an Individual Quantum Dot to a Carbon Nanotube" American Chemical Society pubs.acs.org/NanoLett; DOI: 10.1021/nl102045g | Nano Lett., 2010, 10 (10), pp. 4049-4054.
Syed Arshad Hussain et al.; "An Introduction to Fluorescence Resonance Energy Transfer (FRET)" Department of Physics, Tripura University, Suryamaninagar-799130, Tripura, India; Science Journal of Physics (ISSN:2276-6367), vol. 2012, Article ID sjp-268, 4 Pages, 2012. doi: 10.7237/sjp/268.

* cited by examiner

Fluorescent Change Resulting from Interaction of DCEs (Random DNA) with Phospholipase A2

Fluorescent Change Resulting from Interaction of Individual DCE (Random DNA) with Phospholipase A2

Improved common procedures for interaction, separation, cloning, and sequencing of DCEs with bioagents (just last step)

Fig. 9

BA DCE      Shiga DCE      Tularemia DCE

BA spores or Tularemia agent

Magnetic bead with 60mer random DNA

Washing/H₂O
BA or Tularemia aptamer

Undenatured DCEs

Check fluorescence, running PCR, cloning, and sequencing

Fig. 10
Fluorescent Change Resulting from interactions of S-BA DCE with Bioagents ■ S-BA DCE with BA spores    ● S-BA DCE with Shiga toxin    ▲ S-BA DCE with Tula.agent

Fig. 11

Fluorescent Change Resulting from Interactions of HSA blocked S-Tularemia DCE with agents

▲ HSA block S-Tula.DCE wth BA spores  ● HSA block S-Tula.DCE with Sh.toxin

■ HSA block S-Tula.DCE with Tula.agent

Fig. 15

○-NH〜〜〜〜〜●  ← Aptamer/Fluorophore/Quencher
H○〜〜〜〜〜●     Complex, fluorescence of fluorophore
                 is quenched by quencher ▬ | Botox toxins (A or B, light and heavy chain)

↙ ↘

H○〜〜〜〜〜●           H○〜〜〜〜〜●
                           ▬
+           or            +

○-NH〜〜〜〜〜●         ○-NH〜〜〜〜〜●
    ▬

Fluorescence is dequenched

Fig. 16 Fluorescent Change Resulting from Interactions of Botox aptamer
(type A-light chain, a rapid selection process) with Botox agents ◆ LCA aptamer+LCA agent  ▧ LCA aptamer+HCA agent
▲ LCA aptamer+LCB agent  X LCA aptamer+HCB agent

Fig. 17

Fluorescent Change Resulting from Interaction of Botox aptamer (type B-light chain, rapid selection process) with Botox agents ◆ LCB aptamer+LCA agent  ▓ LCB aptamer+HCA agent ▲ LCB aptamer+LCB agent  X LCB aptamer+HCB agent

Fig. 18

Fluorescent Change Resulting from Interactions of Botox aptamer (type A-light chain, SELEX process) with Botox agents

◆ LCA aptamer+LCA agent ▓ LCA aptamer+HCA agent
▲ LCA aptamer+LCB agent X LCA aptamer+HCB agent

Fig. 19

Fluorescent Change Resulting from Interaction of Botox aptamer (Selected against Botox Holotoxin, SELEX process) with Botox agents

◆ Holo aptamer+LCA agent ▨ Holo aptamer+HCA agent
▲ Holo aptamer+LCB agent X Holo aptamer+HCB agent

Fig. 20

Fluorescent Change from association of Bt aptamer quench system with Bt spores (Sensitivity: 125)

Fig. 21
Fluorescent Change from association of Bt aptamer quench system with Bt spores (Sensitivity: 120)

```
                         SEQUENCE LISTING

<160> NUMBER OF SEQ ID NOS: 25

<210> SEQ ID NO 1
<211> LENGTH: 20
<212> TYPE: DNA
<213> ORGANISM: Artificial Sequence
<220> FEATURE:
<223> OTHER INFORMATION: primary strand

<400> SEQUENCE: 1
acccctgcat cctttgctgg                                                     20

<210> SEQ ID NO 2
<211> LENGTH: 20
<212> TYPE: DNA
<213> ORGANISM: Artificial Sequence
<220> FEATURE:
<223> OTHER INFORMATION: reverse primer

<400> SEQUENCE: 2
agtctagagg gccccagaat                                                     20

<210> SEQ ID NO 3
<211> LENGTH: 110
<212> TYPE: DNA
<213> ORGANISM: Artificial Sequence
<220> FEATURE:
<223> OTHER INFORMATION: primary strand

<400> SEQUENCE: 3
acccctgcat cctttgctgg gcatgtccga tgcgaaccgg atccaatgtc gatcagccgg         60
ttaccgcgct aggtatgtcg atcgctagga agtctagagg gccccagaat                  110

<210> SEQ ID NO 4
<211> LENGTH: 110
<212> TYPE: DNA
<213> ORGANISM: Artificial Sequence
<220> FEATURE:
<223> OTHER INFORMATION: complimentary strand

<400> SEQUENCE: 4
tggggacgta ggaaacgacc cgtacaggct acgcttggcc taggttacag ctagtcggcc         60
aatggcgcga tccatacagc tagcgatcct tcagatctcc cggggtctta                  110

<210> SEQ ID NO 5
<211> LENGTH: 110
<212> TYPE: DNA
<213> ORGANISM: Artificial Sequence
<220> FEATURE:
<223> OTHER INFORMATION: primary strand

<400> SEQUENCE: 5
acccctgcat cctttgctgg gattaacgag taactttggg gcggttgagt tcatggatta         60
aatcaagtat gggtttgccg aagtagccaa agtctagagg gccccagaat                  110

<210> SEQ ID NO 6
<211> LENGTH: 110
```

<212> TYPE: DNA
<213> ORGANISM: Artificial Sequence
<220> FEATURE:
<223> OTHER INFORMATION: complimentary strand

<400> SEQUENCE: 6
tggggacgta ggaaacgacc ctaattgctc attgaaaccc cgccaactca agtacctaat    60
ttagttcata cccaaacggc ttcatcggtt tcagatctcc cggggtctta              110

<210> SEQ ID NO 7
<211> LENGTH: 121
<212> TYPE: DNA
<213> ORGANISM: Artificial Sequence
<220> FEATURE:
<223> OTHER INFORMATION: complimentary strand

<400> SEQUENCE: 7
cccttattct ggggccctct agactttggc tacttcggma aactcatact tgatttaatc    60
catgaactca accgcccaa agttactcgt taaaccccag caaaggrtgc rggggwaagg    120
g                                                                   121

<210> SEQ ID NO 8
<211> LENGTH: 83
<212> TYPE: DNA
<213> ORGANISM: Artificial Sequence
<220> FEATURE:
<223> OTHER INFORMATION: complimentary strand

<400> SEQUENCE: 8
cccttattct ggggccctct agactttggc tacttcmccg cccaaagttc tcgttacccc    60
agcaaaggat gcaggggtaa ggg                                            83

<210> SEQ ID NO 9
<211> LENGTH: 120
<212> TYPE: DNA
<213> ORGANISM: Artificial Sequence
<220> FEATURE:
<223> OTHER INFORMATION: complimentary strand

<400> SEQUENCE: 9
cccttacccc tgcatccttt gctgggcatg tccgatgcga accggatcca atgtcgatca    60
gccggttacc gcgctaggta tgtcgatcgc taggaagtct agagggcccc agaataaggg   120

<210> SEQ ID NO 10
<211> LENGTH: 79
<212> TYPE: DNA
<213> ORGANISM: Artificial Sequence
<220> FEATURE:
<223> OTHER INFORMATION: complimentary strand
<220> FEATURE:
<221> NAME/KEY: misc_feature
<222> LOCATION: (76)..(76)
<223> OTHER INFORMATION: n is a, c, g, or t

<400> SEQUENCE: 10
acccctgcat cctttgctgg agaggaatgt ataaggatgt tccgggcgtg tgggtaatca    60
gtctagaggg ccccanaat                                                 79

<210> SEQ ID NO 11
<211> LENGTH: 80
<212> TYPE: DNA
<213> ORGANISM: Artificial Sequence
<220> FEATURE:

<223> OTHER INFORMATION: DCE sequences

<400> SEQUENCE: 11

```
accccTgcat cctttgctgg agaggaatgt ataaggatgt tccgggcgtg tgggtaagtc    60
agtctagagg gccccagaat                                               80
```

<210> SEQ ID NO 12
<211> LENGTH: 102
<212> TYPE: DNA
<213> ORGANISM: Artificial Sequence
<220> FEATURE:
<223> OTHER INFORMATION: DCE sequences

<400> SEQUENCE: 12

```
accccTgcag gatcctttgc tggtaccact acctaacacc taccttccct cccatcgtcc    60
gctgcacaga gtatcgctaa tcagtctaga gggccccaga at                     102
```

<210> SEQ ID NO 13
<211> LENGTH: 102
<212> TYPE: DNA
<213> ORGANISM: Artificial Sequence
<220> FEATURE:
<223> OTHER INFORMATION: based on Tularemia sequence

<400> SEQUENCE: 13

```
accccTgcag gatcctttgc tggtaccact acctaacacc taccttccct cccatcgtcc    60
gctgcacaga gtatcgctaa tcagtctaga gggccccaga at                     102
```

<210> SEQ ID NO 14
<211> LENGTH: 70
<212> TYPE: DNA
<213> ORGANISM: Artificial Sequence
<220> FEATURE:
<223> OTHER INFORMATION: BoTox aptamers for type A-light chain

<400> SEQUENCE: 14

```
agtctagagg gccccagaat acacccgaca actagatacc catcaaaagt ccagcaaagg    60
atgcaggggt                                                          70
```

<210> SEQ ID NO 15
<211> LENGTH: 70
<212> TYPE: DNA
<213> ORGANISM: Artificial Sequence
<220> FEATURE:
<223> OTHER INFORMATION: BoTox aptamers for type A-light chains

<400> SEQUENCE: 15

```
accccTgcat cctttgctgg acttttgatg ggtatctagt tgtcgggtgt attctggggc    60
cctctagact                                                          70
```

<210> SEQ ID NO 16
<211> LENGTH: 70
<212> TYPE: DNA
<213> ORGANISM: Artificial Sequence
<220> FEATURE:
<223> OTHER INFORMATION: BoTox aptamers for type A-light chain

<400> SEQUENCE: 16

```
accccTgcat cctttgctgg gctatagttg tcaaaacacc tgtgggattg attctggggc    60
cctctagact                                                          70
```

```
<210> SEQ ID NO 17
<211> LENGTH: 70
<212> TYPE: DNA
<213> ORGANISM: Artificial Sequence
<220> FEATURE:
<223> OTHER INFORMATION: BoTox aptamers for type B-light chain

<400> SEQUENCE: 17
agtctagagg gccccagaat tatccactag cgggaagtag tacatctcac ccagcaaagg    60
atgcaggggt                                                          70

<210> SEQ ID NO 18
<211> LENGTH: 70
<212> TYPE: DNA
<213> ORGANISM: Artificial Sequence
<220> FEATURE:
<223> OTHER INFORMATION: selected against BoTox

<400> SEQUENCE: 18
agtctagagg gccccagaat acacccgaca actagatacc catcaaaagt ccagcaaagg    60
atgcaggggt                                                          70

<210> SEQ ID NO 19
<211> LENGTH: 70
<212> TYPE: DNA
<213> ORGANISM: Artificial Sequence
<220> FEATURE:
<223> OTHER INFORMATION: selected against BoTox

<400> SEQUENCE: 19
acccctgcat cctttgctgg acttttgatg ggtatctagt tgtcgggtgt attctggggc    60
cctctagact                                                          70

<210> SEQ ID NO 20
<211> LENGTH: 70
<212> TYPE: DNA
<213> ORGANISM: Artificial Sequence
<220> FEATURE:
<223> OTHER INFORMATION: selected against BoTox

<400> SEQUENCE: 20
agtctagagg gccccagaat tatccactag cgggaagtag tacatctcac ccagcaaagg    60
atgcaggggt                                                          70

<210> SEQ ID NO 21
<211> LENGTH: 70
<212> TYPE: DNA
<213> ORGANISM: Artificial Sequence
<220> FEATURE:
<223> OTHER INFORMATION: selected against BoTox

<400> SEQUENCE: 21
acccctgcat cctttgctgg gtgagatgta ctacttcccg ctagtggata attctggggc    60
cctctagact                                                          70

<210> SEQ ID NO 22
<211> LENGTH: 60
<212> TYPE: DNA
<213> ORGANISM: Artificial Sequence
<220> FEATURE:
<223> OTHER INFORMATION: selected against BoTox

<400> SEQUENCE: 22
```

```
catccgtcac acctgctctg gggatgtgtg gtgttggctc ccgtatcaag ggcgaattct        60

<210> SEQ ID NO 23
<211> LENGTH: 60
<212> TYPE: DNA
<213> ORGANISM: Artificial Sequence
<220> FEATURE:
<223> OTHER INFORMATION: selected against BoTox

<400> SEQUENCE: 23
gtaggcagtg tggacgagac ccctacacac cacaaccgag ggcatagttc ccgcttaaga        60

<210> SEQ ID NO 24
<211> LENGTH: 60
<212> TYPE: DNA
<213> ORGANISM: Artificial Sequence
<220> FEATURE:
<223> OTHER INFORMATION: selected against BoTox

<400> SEQUENCE: 24
catccgtcac acctgctctg ctatcacatg cctgctgaag tggtgttggc tcccgtatca        60

<210> SEQ ID NO 25
<211> LENGTH: 60
<212> TYPE: DNA
<213> ORGANISM: Artificial Sequence
<220> FEATURE:
<223> OTHER INFORMATION: selected against BoTox

<400> SEQUENCE: 25
gtaggcagtg tggacgagac gatagtgtac ggacgacttc accacaaccg agggcatagt        60
```

METHODS AND COMPOSITIONS FOR PROCESSES OF RAPID SELECTION AND PRODUCTION OF NUCLEIC ACID APTAMERS

RELATED APPLICATIONS

This application claims the benefit under 35 U.S.C. §119(e) of U.S. provisional patent application Ser. No. 60/882,454 filed on Dec. 28, 2006 and U.S. provisional patent application Ser. No. 60/989,602 filed on Nov. 21, 2007, both incorporated herein by reference in their entirety.

STATEMENT REGARDING FEDERALLY FUNDED RESEARCH

The U.S. Government has a paid-up license in this invention and the right in limited circumstances to require the patent owner to license others on reasonable terms as provided for by the terms of Contract No. F41624-D-7000 awarded by the United States Air Force.

FIELD

Embodiments herein relate to compositions, systems and methods for making aptamers and/or capture elements. In certain embodiments, compositions, systems and methods herein include making DNA aptamers (DCEs) or RNA aptamers. In some embodiments, methods disclosed herein may be used to rapidly generate large quantities of DNA and/or RNA aptamers directed to a particular target agent. Methods, systems and compositions disclosed herein may be used for detection, identification, collection, decontamination, analysis of disease progression, neutralization, determination of viability, and/or inactivation or killing of such a target agent.

BACKGROUND

Research and use of fluorescent semiconductor nanocrystals (also known as quantum dots or qdots) have evolved over the past several years from electronic materials science to biological applications. Current approaches to the synthesis, solubilization, and functionalization of qdots and their applications to cell and animal biology have grown. Qdots have far-reaching potential for the study of intracellular processes at the single-molecule level, such as high-resolution cellular imaging, long-term in vivo observation of cell trafficking, tumor targeting, and diagnostics.

Aptamers are single-stranded nucleic acids isolated from random-sequence nucleic acid libraries by selection such as in vitro selection. Many DNA or RNA sequences have been isolated that bind a diverse range of targets, including metal ions, small organic compounds, biological cofactors, metabolites, proteins and nucleic acids. The target versatility and the high binding affinity of both DNA and RNA aptamers, their properties of precise molecular recognition, along with the simplicity of in vitro selection, make aptamers attractive as molecular receptors and sensing elements.

Current methods, techniques and devices that have been applied to identification of chemical and biological analytes typically involve capturing the analyte through the use of a non-specific solid surface or through capture deoxyribonucleic acids (DNA) or antibodies. A number of known binding agents must then be applied, particularly in the case of biological analytes, until a binding agent with a high degree of affinity for the analyte is identified such as an aptamer. A labeled aptamer (e.g., labeled DNA) must be applied, where the aptamer causes, for example, the color or fluorescence of the analyte to change if the binding agent exhibits affinity for the analyte (i.e., the binding agent binds with the analyte). The aptamer may be identified by studying which of the various binding agents exhibited the greatest degree of affinity for the analytes.

Some problems associated with current methods of chemical and biological agent identification include that a great deal of time and effort is required to repetitiously generate and apply each of the known labeled aptamers, until an aptamer exhibiting a high degree of affinity is found. In addition, once the identification of a high affinity aptamer is made the synthesis of multiple copies for use becomes a challenge. Accordingly, these techniques are not conducive to easy automation. Current methods are also not sufficiently robust to work in environmental conditions, for example, heat, dust, humidity or other conditions that may be encountered, for example, in the field or in a food processing plant. Portability and ease of use are also problems seen with current methods for chemical and biological agent identification.

There remains a need for methods, systems, and uses for rapidly generating multiple copies of nucleic acid aptamers directed to bind target agents.

SUMMARY

Embodiments herein relate to methods, systems and compositions for rapidly making DNA aptamers (DCE) or RNA aptamers. DNA or RNA aptamers can recognize and associate with a target agent. In certain embodiments, methods herein concern rapid aptamer selection and/or production.

Certain embodiments concern compositions that include double-stranded deoxyribonucleic acid (dsDNA), where a reporter agent is attached to a first strand of the dsDNA sequence and a second strand of the dsDNA has a signal reducing agent capable of quenching the reporter agent. In accordance with these embodiments, the reporter moiety is capable of generating a signal and a signal reducing agent moiety such as a quenching agent (or quenching agent moiety) is capable of reducing or eliminating the signal from the reporter moiety such that observation of the signal generated by reporter is reduced when the complex is in a double stranded form. In another example composition, the reporter moiety and the signal reducing agent moiety can be a distance of about 200 base pairs apart or less, or 150 base pairs apart or less or about 100 base pairs apart or less.

In certain embodiments, a reporter moiety or a signal reducing agent moiety can be non-covalently or covalently bound to a strand of the dsDNA. In certain particular embodiments, a qdot or a quenching agent can be non-covalently or covalently bound to a strand of the dsDNA. In one particular embodiment, a nanostructure, for example a qdot and a quenching agent are covalently bound to opposite strands of a dsDNA molecule.

In certain embodiments, compositions, methods and systems herein concern rapid selection of RNA aptamers. Other embodiments herein concern rapid selection of hybrid molecules such as a double-stranded DNA and associated RNA molecules to make a DNA-RNA hybrid.

Target agents may include, but are not limited to, whole organisms such as a virus, bacteria, or yeast, metal ions, small organic compounds, biological cofactors, metabolites, proteins, nucleic acids, biological warfare agents, terrorism agents, natural or genetically modified agents. In one embodiment, these methods may be used for detection, identification, collection, decontamination, analysis of disease progression, neutralization, determination of viability, inactivation, killing of a target agent or a combination thereof.

Samples contemplated herein can be, but are not limited to, samples from a subject such as human samples, mammalian samples, bird samples or reptile samples (e.g. blood, buccal, nasal, tissue, urine, skin). In some embodiments, a sample can be obtained from a domesticated animal for example, a dog, cat or farm animal. In addition, samples contemplated herein can include one or more samples from an inanimate object including, but not limited to, an air filter, any surface of an object such as a counter, a table, a chair, equipment (e.g. military equipment); or any other surface that a subject may come in contact with; or a sample from a food, soil or water source.

Certain embodiments concern methods for producing capture elements (aptamers), for example DNA capture elements including:

a) contacting a first reagent moiety with a single-stranded nucleic acid sequence mixture to form a first single-stranded complex comprising a ssDNA that is attached to the first reagent moiety; and b) contacting a second reagent moiety with a second ssDNA to form a second ssDNA complex comprising a ssDNA that is attached to the second reagent moiety, wherein the reporter agent moiety comprises a signal producing agent moiety (e.g. a qdot moiety) that is capable of generating a signal or a signal reducing agent moiety (e.g. a quenching agent moiety) that is capable of reducing the signal from the signal producing agent moiety (e.g. a qdot) and the second reagent moiety comprises the other of a signal producing agent moiety or a signal reducing agent moiety.

In one embodiment, the a signal reducing agent moiety is in solution. In another embodiment, a solid substrate can be bound to the strand bound by the signal producing agent moiety.

Some embodiments concern a method for producing aptamers including:

a) contacting a reporter agent moiety with a nucleic acid sequence mixture to form a first nucleic acid sequence-reporter agent moiety complex wherein the reporter agent moiety is covalently or non-covalently attached to the nucleic acid sequence and wherein the reporter agent moiety is capable of producing a signal; and b) contacting a signal reducing agent moiety with a second nucleic acid sequence mixture to form a second nucleic acid sequence-signal reducing agent moiety complex wherein the signal reducing agent moiety is covalently or non-covalently attached to the nucleic acid sequence;

c) introducing the first nucleic acid sequence-reporter agent moiety complexes to the second nucleic acid sequence-signal reducing agent moiety complexes;

d) allowing the complexes to form dsDNA complexes wherein the signal of the reporter agent is reduced in the dsDNA when one strand of the dsDNA contains the reporter agent moiety and one strand of the dsDNA contains the signal reducing agent moiety;

e) introducing a target agent to the dsDNA complexes, wherein the target agent binds to at least one strand of the dsDNA complex to form a target agent-single-stranded DCE complex (target agent-ssDCE complex) when the target agent recognizes at least a portion of the nucleic acid sequence of at least one strand of the dsDNA complex; and f) separating at least a portion of the target agent-ssDCE complex from the remainder of the complexes.

In accordance with this method, the step of separating at least a portion of the target agent-ssDCE complex from the remainder of the complexes can include, but is not limited to, associating the target agent-ssDCE complex with a solid substrate. In addition, associating the target agent-ssDCE complex with a solid substrate can include binding the complex to a complimentary strand of single-stranded DNA bound to a solid substrate.

In a more particular embodiment, methods herein can include amplifying the DCEs of the complex to generate multiple copies of the ssDCEs. In other embodiments, these amplified ssDCEs can be introduced to complimentary sequences and allowed to form double-stranded DCEs. These dsDCEs can be attached to a solid subsurface. In some embodiments, ssDNAs can be used to replicate multiple sequences, partial or entire length sequences from the ssDNA, or generate RNA sequences from the dsDNA or the ssDNA sequences. Alternatively, the ssDCEs, dsDNAs or RNA sequences can also be attached to a solid surface.

In certain embodiments, the reporter moiety can be a qdot and the signal reducing moiety can be a quenching agent. In other embodiments, the first reagent moiety can be an enzyme capable of producing a signal and the second reagent moiety can be a reversible inhibitor of the enzyme. In accordance with these methods, the signal can include but is not limited to, a detectible product, or a chemical change such as a colorimetric change. In some embodiments, the reporter agent moiety can include, but is not limited to an enzyme, for example, peroxidase or alkaline phosphatase. In certain embodiments, the quenching agent can be, but is not limited to, an inhibitor, for example, an aptamer or a small molecule inhibitor attached to the aptamer.

In some embodiments, other reporters of use herein can include, but are not limited to, halogen conjugates (e.g. Iodine, Bromine, Fluorine etc.) of the aptamers or calixarenes conjugates. In some embodiments, DALM can be associated with aptamers generated or identified herein. In accordance with these methods, these aptamers can be used to capture various metals (rare earths to common metals like potassium and sodium) or as markers of each strand of the double-stranded aptamer. These ions can be detected by atomic absorption spectra like that generated by laser induced breakdown and measured by a spectrometer; when the double strands are joined the ionic spectral emissions are in a fixed proportion. In one exemplary method, if one strand (complementary strand) is displaced and essentially removed, the aptamer remains and the one metal or ion signal of the aptamer strand, with the other reduced (depending on the amount of displacement), or, with maximal displacement gone.

In more particular embodiments, if the inhibitor was an indicator enzyme, then when a target for another aptamer attached to an inhibitory aptamer bound to its target, the reaction would displace the inhibitor aptamer from the indicator enzyme on the complementary strand. In further embodiments, the enzyme could be, for example, a calorimetric or fluorescent substrate. In certain particular examples, the substrate may be ABTS for peroxidase; nitrophenyl phosphate, BCIP, Fast Red, Fuchsin for alkaline phosphatase or a combination thereof, or a mixture thereof.

Certain embodiments of these methods can utilize a solid surface including, but not limited to, glass, plastic, silicon-coated substrate, macromolecule-coated substrate, particles, beads, microparticles, microbeads, dipstick, magnetic beads, paramagnetic beads and a combination thereof. In some embodiments, a solid surface can be used to immobilize a capture element disclosed herein. In other embodiments, a solid surface can be used to immobilize single-stranded sequences complimentary to a ssDCE of a target agent-ss- DCE complex. In yet other embodiments, a solid surface can be used to immobilize RNA aptamers or hybrid aptamers such as RNA and DNA.

Other embodiments include a system for producing DNA aptamers including:

a) an element for inputting a first reagent with a first mixture of nucleic acid sequences to form a first reagent-nucleic acid sequence complex in a reaction vessel; and b) an element for inputting a second reagent with a second mixture of nucleic acid sequences to form a second reagent-nucleic acid sequence complex in another reaction vessel; wherein the first reagent comprises a signal producing agent moiety or a reversible signal reducing agent moiety or reversible signal eliminating agent moiety and the second reagent comprises the other of a signal producing agent moiety, or a reversible signal reducing agent moiety or reversible signal eliminating agent moiety.

Certain embodiments can include a system having a first reagent that includes a qdot moiety or a quenching agent moiety and the second reagent including the other of a qdot moiety or a quenching agent moiety.

In another embodiment, a system can further include an element for partitioning the dsDNA complex from the remainder of the mixture and/or include an element for partitioning the second dsDNA complex from the remainder of the mixture. In addition, systems can further include:

c) an element for mixing the first reagent-nucleic acid sequence complex with the second reagent-nucleic acid sequence complex in a reaction vessel to form a dsDNA complex;

d) an element for inputting a target agent to the dsDNA complex to form a target agent-single stranded DCE complex (target agent-ssDCE complexes) wherein the target agent-ssDCE complexes are formed when the target agent binds to at least one strand of the dsDNA complex separating the dsDCE complex into single-stranded nucleic acid sequences (ssDCE).

In another embodiment, a system can further include:

e) an element for separating the target agent-ssDCE complexes from the remainder of the complexes using a solid substrate wherein the target agent-ssDCE complex is bound directly or indirectly to the solid substrate; and f) an element for amplifying the ssDCE bound to the solid substrate.

In other embodiments, systems contemplated herein can be used to generate and/or isolate RNA aptamers and/or hybrid molecule aptamers.

Another embodiment can include a composition of a quenching agent moiety bound to a dsDNA sequence wherein adsorption wavelength of the quenching agent moiety overlaps with emission wavelength of an agent capable of generating a signal.

In other embodiments, a solid substrate may include, but are not limited to beads, microbeads, spheres, slides, dipsticks, dishes, microwell plates, particles, microparticles, nanoparticles or combination thereof. In accordance with these embodiments, the beads or particles can be selected from the group, including but not limited to, paramagnetic beads, magnetic beads, superparamagnetic beads, streptavidin coated beads, Reverse Phase magnetic beads, carboxy terminated beads, hydrazine terminated beads, Silica (sodium silica) beads and IDA (iminodiacetic acid) modified beads, aldehyde modified beads, Epoxy activated beads, DADPA-modified beads (beads with primary amine surface group), biodegradable polymeric beads, amino-polystyrene particles, carboxyl-polystyrene particles, Epoxy-polystyrene particles; dimethylamino-polystyrene particles, hydroxy-polystyrene particles, colored particles, flow cytometry particles, and sulfonate-polystyrene particles.

In certain embodiments, the nucleic acid sequences may be sequences of 1 to 1000, 10 to 500, 10 to 250, 10 to 150, 10 to 75, 20 to 60, 15 to 45, 20 to 40 base pairs in length, a single length, a combination of lengths or mixture thereof or combination thereof.

In another embodiment, amplification of molecules that bind a target agent can be used to generate multiple copies of the DCEs (aptamers), hybrid molecules or RNA aptamers (e.g. RNA aptamers) that bind a target agent. Methods useful for amplifying the partitioned sequences may include, but are not limited to, polymerase chain reaction (PCR), the ligase chain reaction (LCR) Qbeta Replicase, an isothermal amplification method, Strand Displacement Amplification (SDA), Repair Chain Reaction (RCR), transcription-based amplification systems (TAS), including nucleic acid sequence based amplification (NASBA) and 3SR.

In another embodiment, DCEs may be generated to a target agent and used to analyze the presence of the target agent in a sample from a subject suspected of containing the target agent. In accordance with this exemplary use, DCEs directed to bind the target agent can be combined with the sample and the sample can be analyzed for the presence, absence or level of the target agent based on association with the aptamers.

Some embodiments include kits for generating and using compositions and methods disclosed herein. For example a kit can include, at least one container, a solid phase composition, a solid phase separation unit, a signal reducing agent composition, a signal producing agent composition; and at least one control sample. In addition, the kit can include a sample composition of a mixture of 1 to 1000, 10 to 500, 10 to 250, 10 to 150, 10 to 75, 20 to 60, 15 to 45, 20 to 40 or a combination of base pair lengths of nucleic acid sequences and/or a target agent compositions. In some embodiments, kits may contain DCEs, hybrid aptamer molecules, RNA aptamers or a combination of two or more aptamers capable of binding one or more target molecules. Example kits may include one or more DCEs capable of binding one or more target molecule able to detect, identify, decontaminate, analyze disease progression, neutralize, determine viability, inactivate, kill or combination thereof. In some embodiments, a kit may be generated for both detecting and destroying, detecting and decontaminating, detecting and identifying one or more target agents. Certain kits are directed to particular target molecules and the target molecules can include, but are not limited to, whole organisms such as a virus, yeast, protoplasts, prions or bacteria; metal ions; small organic compounds; biological cofactors; metabolites; proteins; nucleic acids; biological warfare agents; terrorism agents; natural or genetically modified agents or a combination thereof. In one embodiment, these methods may be used for detection, identification, collection, decontamination, analysis of disease progression, neutralization, determination of viability, inactivation, killing of a target agent or a combination thereof. In some embodiments, a kit can be used to generate aptamers from methods and compositions disclosed herein. In certain embodiments, a kit can contain aptamers disclosed herein and can be used to assess the presence and/or level of a target agent in a sample from a subject suspected of having or at risk for developing a disorder where the target agent is indicative of the onset, progression or existence of the disorder. In another embodiment, a kit can include a quantum dot agent moiety composition and a quenching agent moiety composition.

BRIEF DESCRIPTION OF THE DRAWINGS

The following drawings form part of the present specification and are included to further demonstrate certain embodiments. The embodiments may be better understood by reference to one or more of these drawings in combination with the detailed description of specific embodiments presented herein.

FIG. 9 represents an exemplary flow chart depicting an exemplary solid phase technology capable of performing embodiments of the disclosed methods.

FIG. 10 represents an exemplary graph depicting fluorescent level changes versus time.

FIG. 11 represents an exemplary graph depicting fluorescent levels versus time.

FIG. 15 represents an exemplary schematic of an interaction of aptamer/fluorophore/quencher complexes with BoTox agents.

FIG. 16 represents an exemplary graph depicting fluorescent level changes from interaction of BoTox aptamers (selected against type A-light chain) with Botox toxin versus time.

FIG. 17 represents an exemplary graph depicting fluorescent level changes from interaction of BoTox aptamers (selected against type B-light chain) with Botox toxin versus time.

FIG. 18 represents an exemplary graph depicting fluorescent level changes from interaction of BoTox aptamers (selected against type A-light chain) with botox toxin versus time.

FIG. 19 represents an exemplary graph depicting fluorescent level changes from interaction of BoTox aptamers (selected against BoTox Holotoxin, SELEX Process) with Botox toxin versus time.

FIG. 20 represents an exemplary graph depicting fluorescent level changes from interaction of Bt aptamer quench system with Bt spores (sensitivity 125).

FIG. 21 represents an exemplary graph depicting fluorescent level changes from interaction of Bt aptamer quench system with Bt spores (sensitivity 120).

DESCRIPTION OF ILLUSTRATIVE EMBODIMENTS

Definitions

Figure 1:
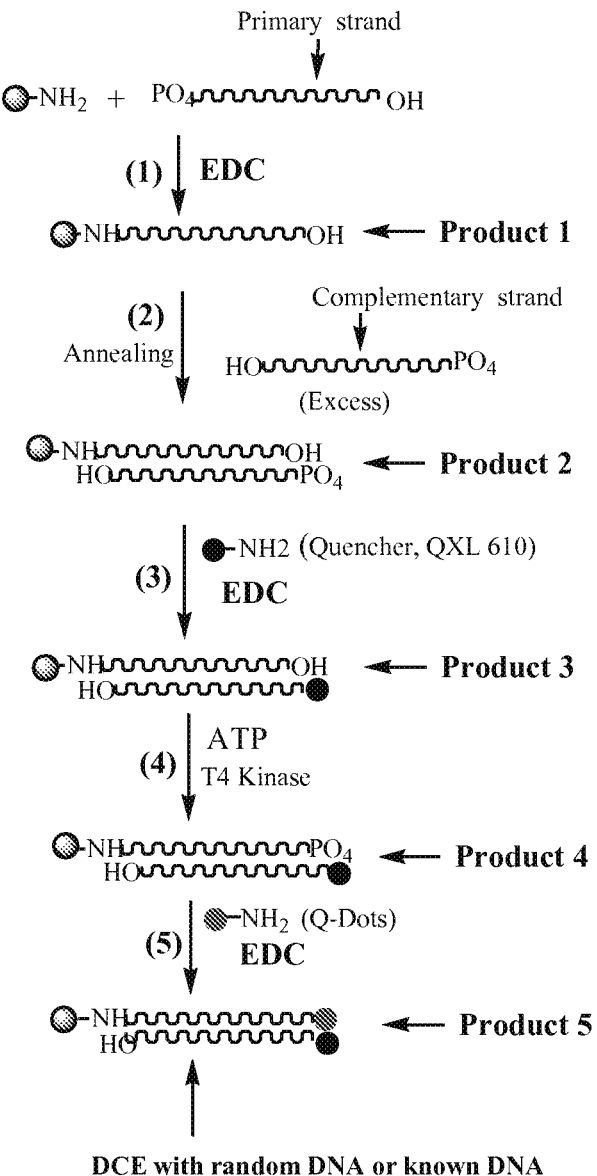
FIG. 1 represents an exemplary flow chart depicting generation of a double-stranded sequence having a quantum dot (qdot) and a quenching agent.
Figure 2:
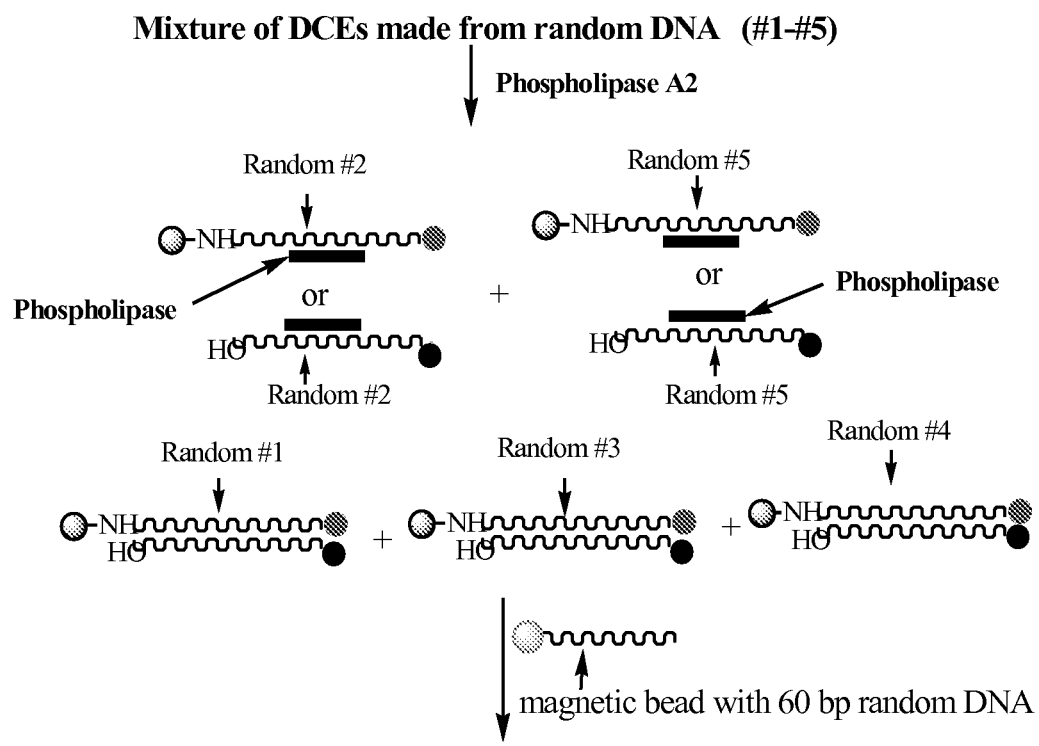
FIG. 2 represents an exemplary flow chart depicting isolation of nucleic acid sequences that associate with a target agent.
Figure 3:
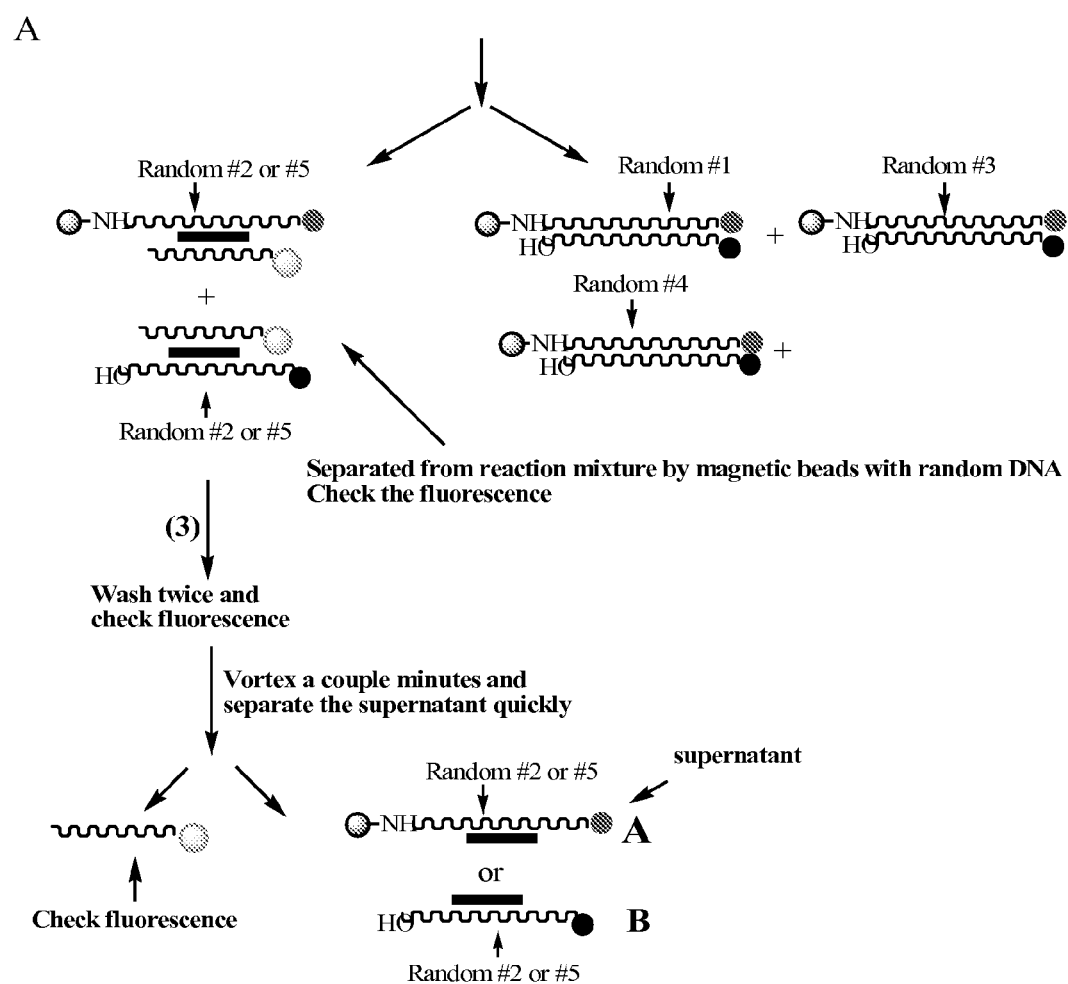
FIG. 3 represents an exemplary flow chart depicting isolation and subsequent amplification of single stranded nucleic acid sequences capable of associating with a target agent.
Figure 4:
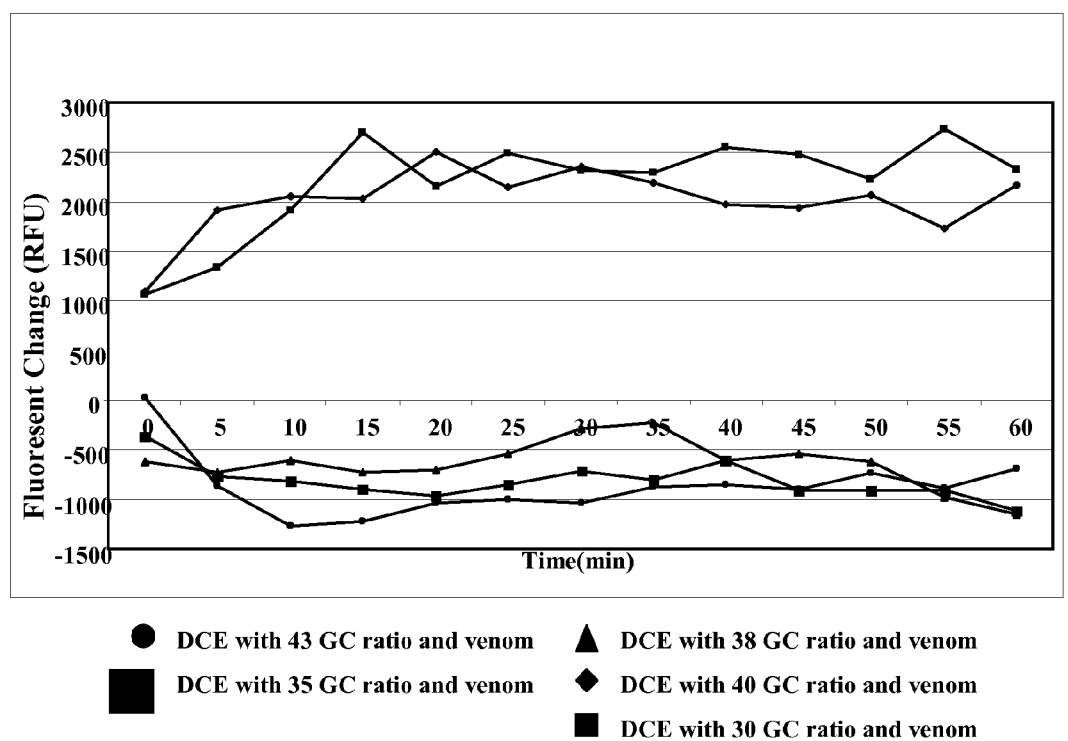
FIG. 4 represents an exemplary graph depicting fluorescent level changes versus time.
Figure 5:
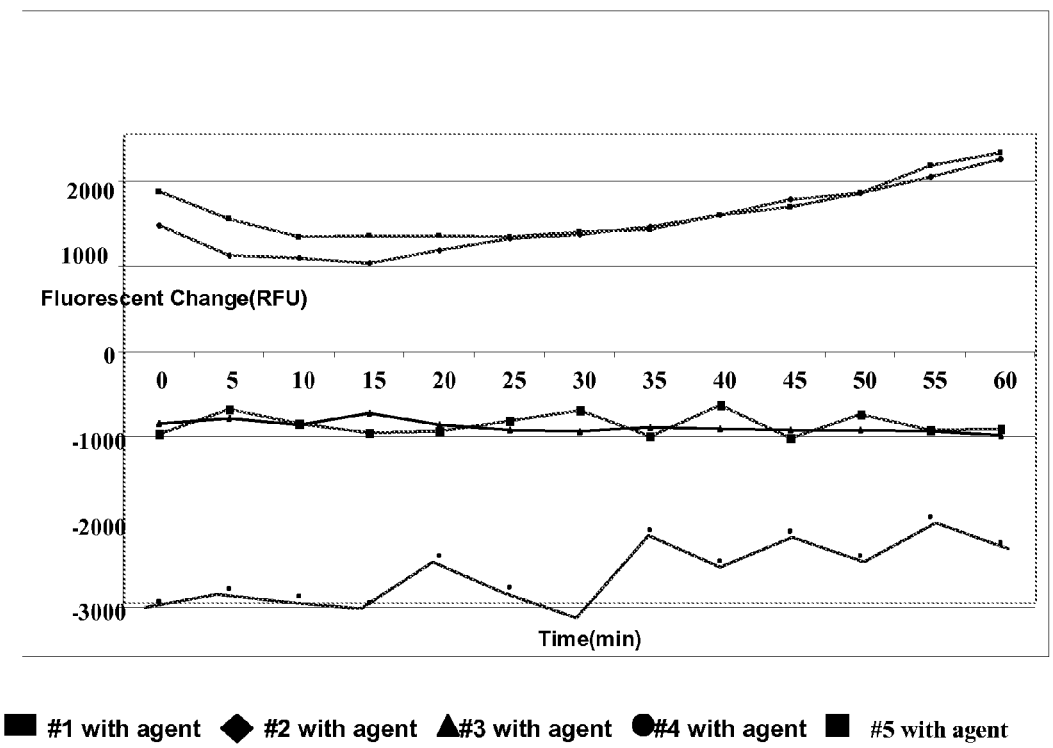
FIG. 5 represents an exemplary graph depicting fluorescent level changes versus time.
Figure 6:
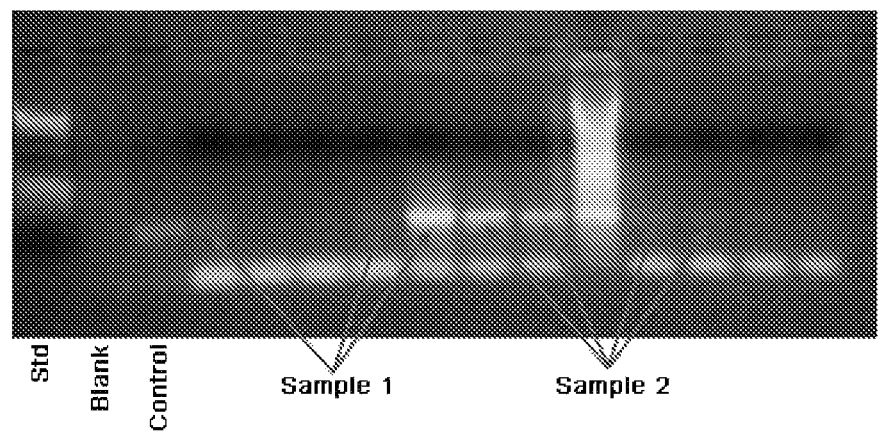
FIG. 6 represents an exemplary electrophoresis gel depicting DCE samples after amplification.
Figure 7A:
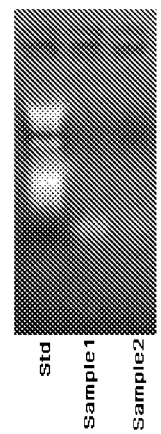
FIGS. 7A-7C represents an exemplary electrophoresis gel depicting DCE samples after amplification.
Figure 7B:
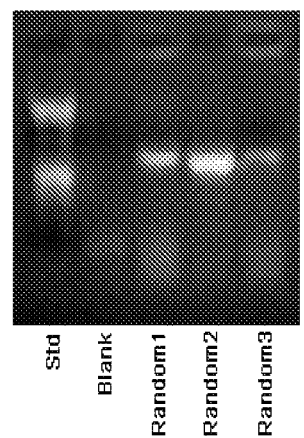
Figure 7C:
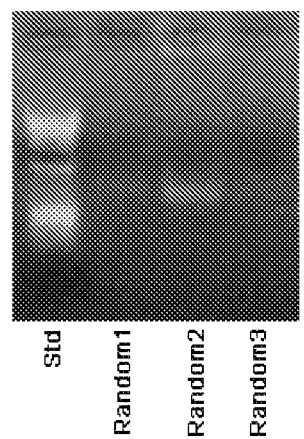
Figure 8A:
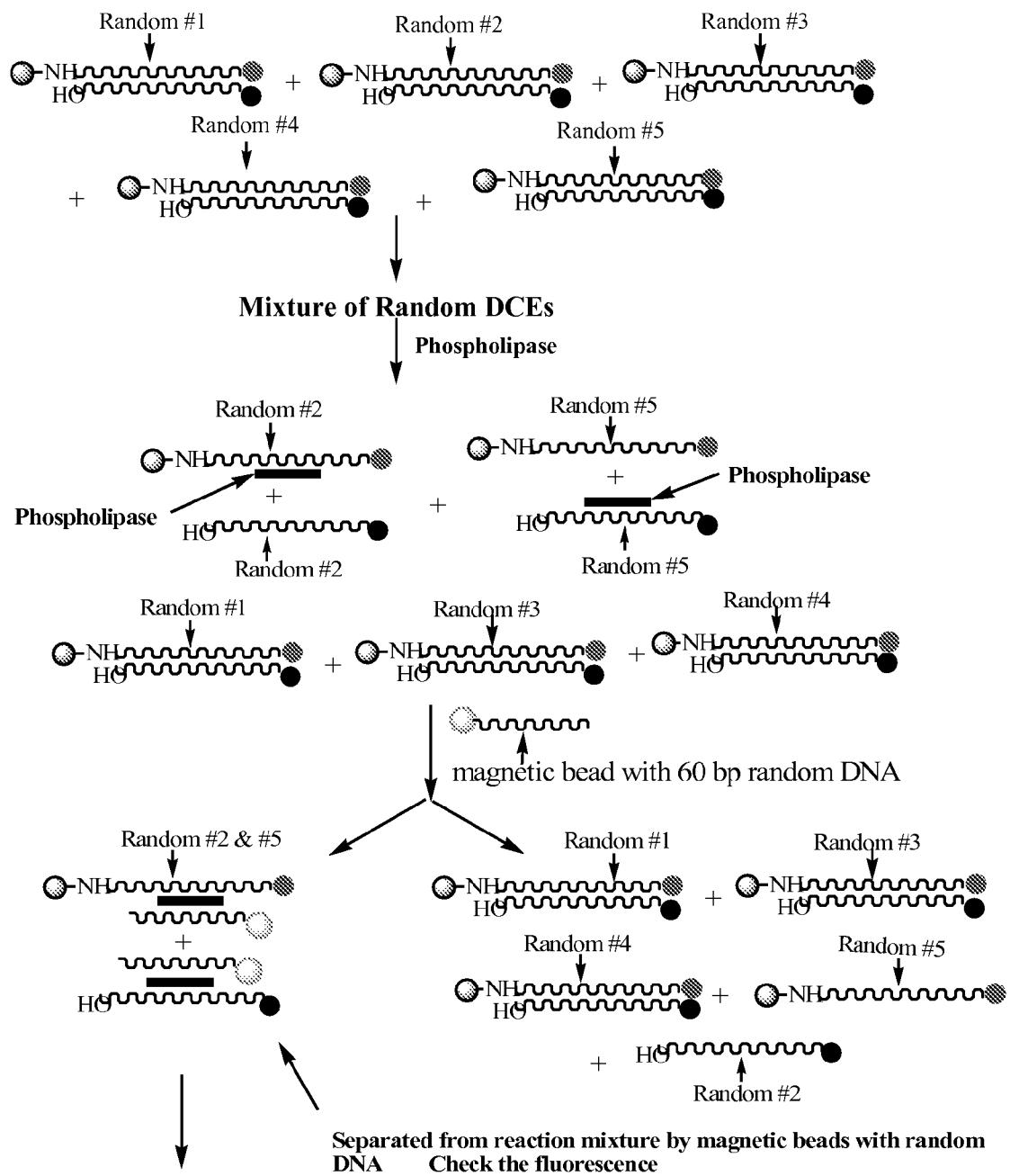
FIGS. 8A-8C represents an exemplary flow chart depicting isolation of nucleic acid sequences that associate with a target agent.
Figure 8B:
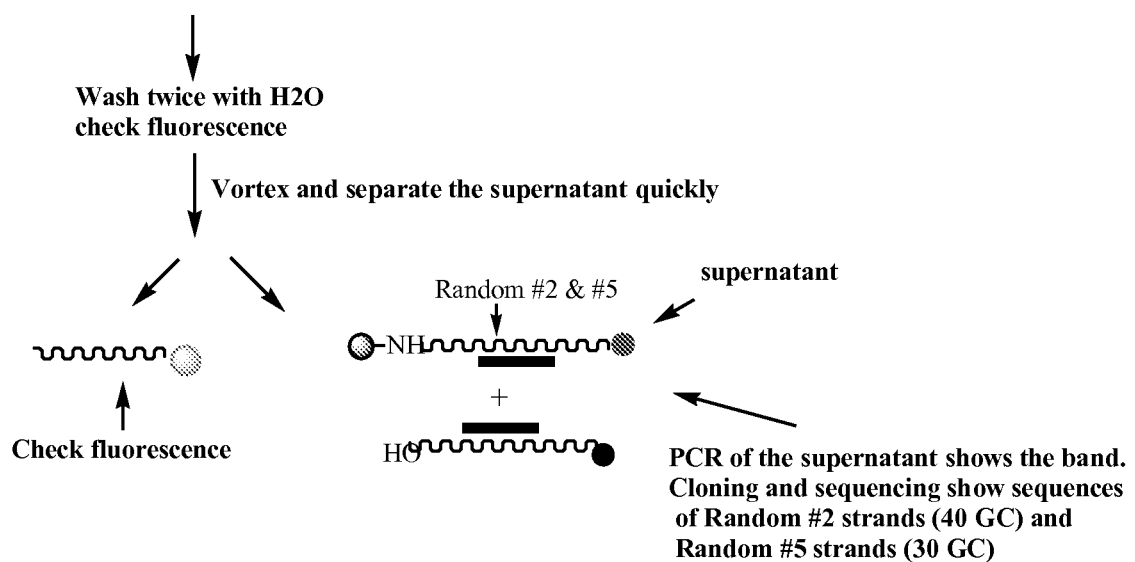
Figure 8C:
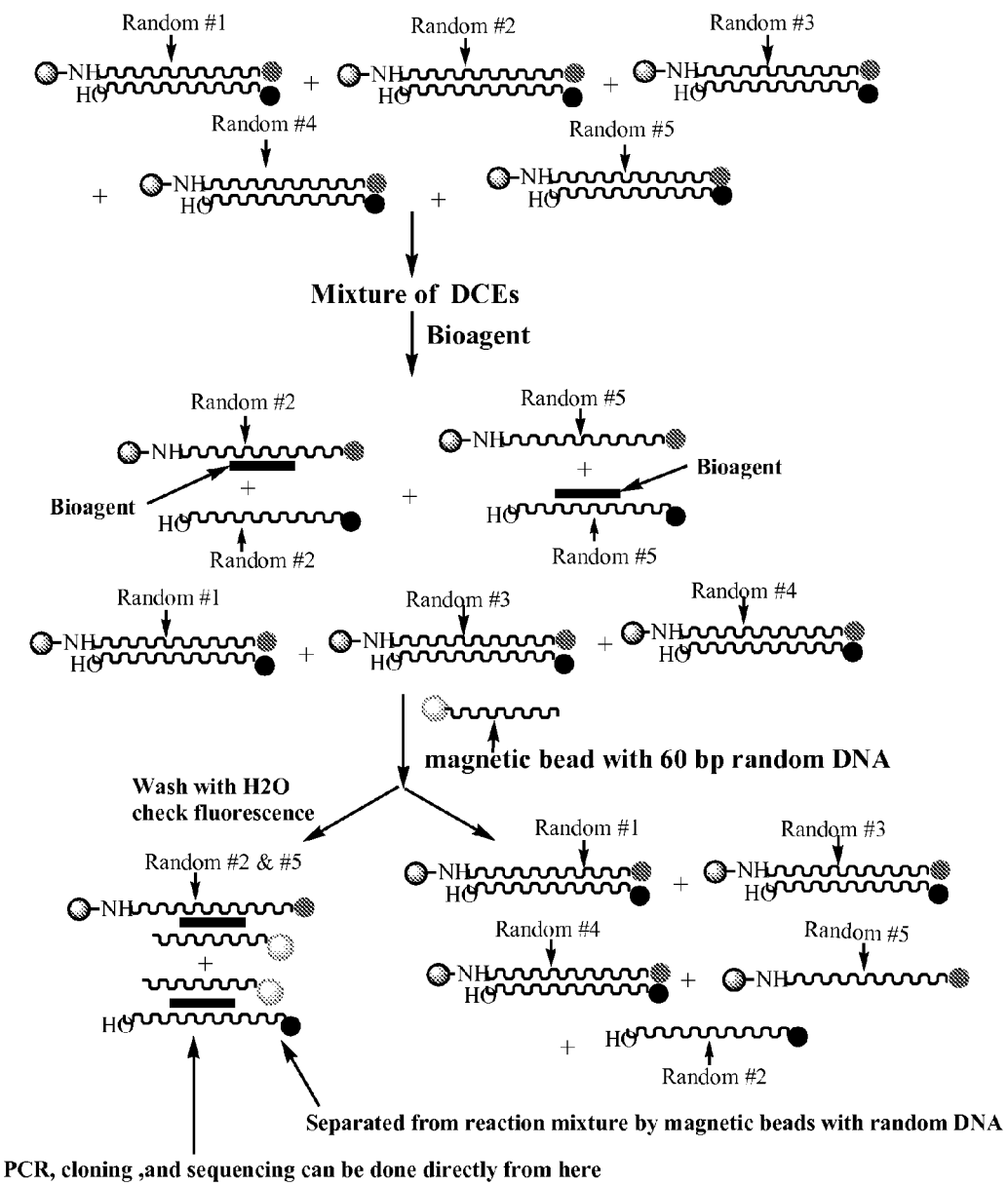

As used herein, "a" or "an" may mean one or more than one of an item.

"Nucleic acid" means either DNA, RNA, single-stranded, double-stranded, hybrid molecules such as RNA/DNA or triple stranded and any chemical modifications thereof. Virtually any modification of the nucleic acid is contemplated herein. Non-limiting examples of nucleic acid modifications are discussed in further detail below. "Nucleic acid" encompasses, but is not limited to, oligonucleotides and polynucleotides. "Oligonucleotide" refers to at least one molecule of between about 3 and about 100 nucleotides in length. "Polynucleotide" refers to at least one molecule of greater than about 100 nucleotides in length. These terms generally refer to at least one single-stranded molecule, but in certain embodiments also encompass at least one additional strand that is partially, substantially or fully complementary in sequence. Thus, a nucleic acid may encompass at least one double-stranded molecule or at least one triple-stranded molecule that comprises one or more complementary strand(s) or "complement(s)." As used herein, a single stranded nucleic acid may be denoted by the prefix "ss", a double stranded nucleic acid by the prefix "ds", and a triple stranded nucleic acid by the prefix "ts."

Within the practice disclosed herein, a "nucleic acid" may be of almost any length, from 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 40, 45, 50, 55, 60, 65, 70, 75, 80, 85, 90, 95, 100, 110, 120, 130, 140, 150, 160, 175, 200, 225, 250, 275, 300, 400, 500, 600, 700, 800, 900, 1000, 1500, 2000, 2500, 3000, 3500, 4000, 4500, 5000, 6000, 7000, 8000, 9000, 10000, 15000, 20000 or even more bases in length. In some embodiments, nucleic acid sequences may be around 10 to around 200 bases in length. In other embodiments, double-stranded DNA molecules (dsDNA) may be around 2 to 1000, 10 to 500, 10 to 250, 10 to 150, 10 to 75, 20 to 60, or 15-45 base pairs in length.

The term "nucleic acid" as used herein can generally refer to at least one molecule or strand of DNA, RNA or a derivative or mimic thereof, comprising at least one nucleobase. A "nucleobase" refers to a heterocyclic base, for example, a purine or pyrimidine base naturally found in DNA (e.g. adenine "A," guanine "G," thymine "T" and cytosine "C") or RNA (e.g. A, G, uracil "U" and C), as well as their derivatives and mimics. A "derivative" refers to a chemically modified or altered form of a naturally occurring molecule, while "mimic" and "analog" refer to a molecule that may or may not structurally resemble a naturally occurring molecule, but that function similarly to the naturally occurring molecule. One function of a nucleobase is to hydrogen bond to other nucleobases. Nucleobases can form one or more hydrogen bonds ("anneal" or "hybridize") with at least one naturally occurring nucleobase in manner that may substitute for naturally occurring nucleobase pairing (e.g. the hydrogen bonding between A and T, G and C, and A and U).

A nucleic acid may include, or be composed entirely of, at least one nucleobase, a nucleobase linker moiety and/or a backbone moiety.

As used herein, a "moiety" generally can refer to a smaller chemical or molecular component of a larger chemical or molecular structure, and is encompassed by the term "molecule." In some embodiments, a moiety can be a component of a larger molecule, for example, a reporter agent moiety or a signal reducing agent moiety.

A "nucleotide" as used herein can mean a nucleoside further comprising a "backbone moiety" used for the covalent attachment of one or more nucleotides to another molecule or to each other to form a nucleic acid. The "backbone moiety" in naturally occurring nucleotides typically comprises a phosphorus moiety covalently attached to a 5-carbon sugar. The attachment of the backbone moiety typically occurs at either the 3'- or 5'-position of the 5-carbon sugar. However, other types of attachments are known in the art, particularly when the nucleotide comprises derivatives or mimics of a naturally occurring 5-carbon sugar or phosphorus moiety.

"DNA capture element" (DCE), "RNA capture element", or hybrid capture element or "aptamer," as used herein can mean non-naturally occurring nucleic acid molecules (such as nucleic acid sequences) having a desirable action on a target agent. In some embodiments, one desirable action can include, but is not limited to, binding of a target agent, reacting with a target agent in a way that modifies or alters the target agent or the functional activity of the target agent, covalently attaching to the target agent, facilitating the reaction between the target agent and another molecule, killing the target agent and/or neutralizing the target agent. In other embodiments, the action can be specific binding affinity for a target agent, such target agent being a three dimensional chemical structure. The meaning of "DCE" includes nucleic acids that bind to other nucleic acids. In one particular embodiment, binding of a DCE to a target agent allows recognition, quantitation and/or neutralization of the target agent. Capture elements or aptamers herein include, but are not limited to, nucleic acids that are generated and/or identified by methods and compositions disclosed herein. Binding interactions of a DCEs or aptamers may not encompass standard nucleic acid/nucleic acid hydrogen bond formation exemplified by Watson-Crick basepair formation (e.g., A binds to U or T and G binds to C), but may encompasses all other types of non-covalent (or in some cases covalent) binding. Non-limiting examples of non-covalent binding include hydrogen bond formation, electrostatic interaction, Van der Waals interaction and hydrophobic interaction. A DCE or any other aptamer contemplated herein may bind to another molecule by any or all of these types of interaction, or in some cases by covalent interaction. Covalent binding of a DCE to another molecule may occur where the DCE or target molecule contains a chemically reactive or photoreactive moiety. The term DCE can include a DNA capture element that is capable of forming a complex with an intended target agent. "Target-specific" means that the DCE binds to a target agent with a much higher degree of affinity than it binds to other materials.

"Analyte," "target," "target agent" and "target analyte" as used herein can mean any compound, whole organism, object, or aggregate of interest. Non-limiting examples of target agents can include, but are not limited to, a whole organism (e.g. bacteria, yeast or virus); protein, peptide, carbohydrate, polysaccharide, glycoprotein, lipid, hormone, receptor, antigen, allergen, antibody, substrate, metabolite, cofactor, enzyme, metal ion, inhibitor, drug, pharmaceutical, nutrient, toxin, poison, explosive, pesticide, chemical warfare agent, biohazardous agent, prion, radioisotope, vitamin, heterocyclic aromatic compound, carcinogen, mutagen, narcotic, amphetamine, barbiturate, hallucinogen, waste product, contaminant or other molecule. Molecules of any size can serve as targets. "Target agents" are not limited to single molecules, but may also comprise complex aggregates of molecules, such as a virus, bacterium, spore, mold, yeast, algae, amoebae, dinoflagellate, unicellular organism, pathogen or cell. In certain embodiments, a sample suspected of having a particular bacterium present, such a pathogenic bacteria, may target analytes. Virtually any chemical or biological effector would be a suitable target.

"Binding" as used herein can mean an interaction, association or binding between a target agent and an aptamer, resulting in a sufficiently stable complex so as to permit separation of aptamer: target complexes from uncomplexed aptamers under given binding or reaction conditions. Binding is mediated through hydrogen bonding or other molecular forces.

"DCE Recognition complex" or "RNA capture element complex" as used herein can mean a DCE or RNA capture element that is operably coupled to a reporter agent, qdot or equivalent molecule thereof (e.g. another agent capable of producing a signal or having an assayable activity). For example, "Operably coupled" can mean that the DCE or aptamer and the qdot are in close physical proximity to each other, such that binding of an analyte or target agent to the DCE or aptamer results in a detectable target agent as a signal or other detectible means. In one particular embodiment, the signal is an electrochemical. "Electrochemical" as used herein can mean used in a broad sense to mean any process involving a transfer of electrons, including reduction-oxidation chemistry of any sort. "Electrochemical" specifically includes photo-induced oxidation and reduction. In other embodiments, a signal may include a photochemical signal, a fluorescent signal, a luminescent signal, or a change in electrical conductivity. In another embodiment, the signal is a change in the fluorescence emission profile of an aptamer or DCE Recognition complex. In yet other embodiments, the signal may be detecting enzymatic activity or enzymatic inhibition of activity. In other embodiments, the signal can be a chemical such as a change of color.

"Signal producing agent moiety" or "reporter agent moiety" or "reporter agent" as used herein can mean a moiety capable of producing a detectible signal such as a detectible enzymatic product or detectible signal such as emission of light (e.g. fluorescence or visible light, qdot).

"Signal reducing agent moiety" or "signal eliminating agent moiety" or "signal reducing agent" as used herein can mean a moiety capable of lowering the signal or eliminating a signal produced from a signal producing agent moiety or reporter agent moiety from detection (e.g. quenching agent).

In certain embodiments, operable coupling may be accomplished by a variety of interactions, including but not limited to, non-covalent or covalent binding of the detectible agent to an aptamer. Virtually any type of interaction between a detectible agent and an aptamer is contemplated within the scope herein. Aptamer Recognition complexes result in a detectible complex bound to the target agent. In certain embodiments, a quantum dot may be bound to a DCE.

In other embodiments, a quantum dot may be linked to a DCE. In accordance with these embodiments, the quantum dot can be linked through a phosphate group or a carboxyl group found on the quantum dot molecule or any other means capable of forming a link to a DCE. A quantum dot may be chosen for a specific functional group on the qdot for attaching to the end of a DCE molecule or to a specific site within the DCE molecule. It is contemplated herein that a quenching agent within a certain distance of a qdot will result in reduced or complete quenching of a signal produced by the qdot. In some embodiments, it is contemplated that a quenching agent and the qdot can be within whatever distance is necessary depending upon the circumstances or conditions to maintain quenching or about 1.0 nm to 1 cm from one another, 1.0 nm to 0.2 cm from one another, 1 nm to 50 nm from one another, or a few millimeters to a few nanometers from one another. In certain embodiments, the quenching agent and the qdot may be about 1.0 to about 30 nm apart from one another.

Quenching agents contemplated for use in any of the disclosed embodiments include, but are not limited to QXL™ quenchers (e.g. AnaSpec. Inc., San Jose Calif.) such as QXL™ 610, QXL™ 490 acid, Abs/Em=485/none nm; QXL™ 490 C2 amine, Abs/Em=485/none nm; QXL™ 520 C2 amine, Abs/Em=530/none nm; QXL™ 570 C2 amine, Abs/Em=577/none nm; QXL™ 670 C2 amine, Abs/Em=668/none nm; QXL™ 680 C2 amine, Abs/Em=679/none nm; DNP C2 amine, Abs/Em=350/none nm; and DABSL quenchers, such as, DABSYL-L-alanine, Abs/Em=436/none nm; DNP C2 amine, Abs/Em=350/none nm. DABCYL Plus™ C2 amine, Abs/Em=430/none nm; Boc-Lys(DABCYL)-OH, Abs/Em=428/none nm. In one embodiment, the quenching agent comprises an agent having an adsorption wavelength that overlaps with emission wavelength of quantum dots bound to a sequence of interest.

Additional quenching agents contemplated of use in any of the disclosed embodiments include, but are not limited to BHQ quenchers (e.g. Biosearch Technologies). BHQ's are organic molecules that can efficiently quench fluorescence emissions in the visible, as well as into the near IR. These molecules possess no native fluorescence, thus no background fluorescence needs to be accounted for from the BHQ quenchers. Therefore, the signal to noise ratio increases compared to other quenchers available. Other quenching agents contemplated of use in any of the disclosed embodiments herein can include, but are not limited to, Dabcyl/Dabsyl and QSY.

In certain embodiments, it is contemplated that other detectible agents or reactions or inhibitors may be of use as quality control for making and using DCEs and/or other aptamers contemplated herein. Recognition complex as used herein can mean an aptamer or DCE that is operably coupled to an enzyme or equivalent molecule thereof (e.g. another agent capable of producing a signal or having an assayable activity) in certain circumstances to monitor the making of aptamers by processes disclosed herein. The aptamer can be operably coupled to an enzyme and an inhibitor of the enzyme where the aptamer and enzyme are in close physical proximity to each other, such that binding of an analyte or target agent to the aptamer results in a detectable agent as a signal, enzymatic reaction (e.g. where the reaction results a detectible product being produced or a detectible signal) or other detectible means. In one particular embodiment, an enzyme inhibitor is a reversible inhibitor is an enzymatic reaction. Reversible inhibitors bind to the enzyme using weak bonds, similar to those used in binding a substrate. These bonds are formed rapidly, but also break easily. Reversible inhibitors can effectively be instantaneous in their action, but do not permanently inactivate the enzyme. In accordance with these embodiments, a double-stranded complex disclosed herein may have one strand that is bound to an enzyme and the other strand could be bound by an inhibitor of the enzyme and when the complex is double-stranded the enzyme is inactive. In this example, a target agent that binds to and separates a double-stranded molecule into single-stranded regions to form a target agent-aptamer complex could be detectible by observing enzyme activity, for example, production of a product by catalytic action of an enzyme or chemical conversion of a substrate of an enzyme.

In other embodiments, a DCE Recognition complex or other aptamer recognition complex can include color detection, color change or color amplification similar to colorometric assay systems known in the art (e.g. colormetric assays such as alkaline phosphotase-based assays and DNA modifying enzymes assays found for example at R & D Systems, U.S.A.). In certain embodiments, colorometric detection or change indicates the presence of a target-agent-aptamer complex allowing isolation of the complex (e.g. for amplification of the aptamer).

A "DCE Recognition complex" as used herein can mean an array of recognition complexes. In preferred embodiments, the array of recognition complexes is operably coupled to a detection unit, such that binding of a recognition complex to a target agent may be detected by the detection unit. It is contemplated within the scope herein that detection may be an active process or a passive process. For example, in embodiments where the array of recognition complexes is incorporated into a card, badge, reader, dipstick, assay kit or the like the binding of a target agent by a DCE recognition complex may be detected by a change in color or readily readable fluorescence of the card, badge, reader, dipstick, assay kit or the like. In other embodiments, detection occurs by an active process, such as scanning the fluorescence emission profile of an array of recognition complexes.

"Photochemical" as used herein can mean any light related or light induced chemistry. A "photochemical signal" specifically includes, but is not limited to, a fluorescent signal, a luminescent signal, a change of color, a change in electrical conductivity, photo-oxidation and photo-reduction.

"Magnetic bead," "paramagnetic bead," "nanoparticle," "magnetic particle" and "magnetically responsive particle" as used herein can mean any particle dispersible or suspendable in aqueous media, without significant gravitational settling and separable from suspension by application of a magnetic field.

"Bound," as used herein can mean covalently or non-covalently associated with a molecule. For example, a quantum dot bound to a nucleic acid sequence can be a quantum dot covalently or non-covalently associated with the nucleic acid sequence.

In the following sections, several embodiments of, for example, compositions and methods are described in order to thoroughly detail various embodiments herein. It will be obvious to one skilled in the art that practicing the various embodiments does not require the employment of all or even some of the specific details outlined herein, but rather that concentrations, times and other specific details may be modified through routine experimentation. In some cases, well known methods or components have not been included in the description to prevent unnecessary masking of various embodiments.

There is a need for the development of compositions, methods and apparatus capable of synthesizing agents capable of detecting and identifying target agents such as chemical and biological agents which include, but are not limited to, nucleic acids, proteins, metal ions, small organic compounds, biological cofactors, metabolites, illicit drugs, explosives, toxins, pharmaceuticals, carcinogens, poisons, allergens, whole organisms, biological warfare agents, terrorism agents, natural or genetically modified agents and infectious agents. One solution may include the use of nucleic acid binding agents and recognition technologies and/or isolation methods such as magnetic bead technologies. In one embodiment, methods and compositions provide a novel and unexpected advancement of these technologies to synthesize, detect, isolate and/or identify DCEs known to associate with for example, chemical and biological agents.

In some embodiments, aptamers are contemplated of use against viral, yeast and bacterial organisms. In certain embodiments, aptamers can be made to recognize at least one of the following, ions, antibiotics, small molecules, RNA structures, proteins, receptors, viruses and cells up to whole organisms are contemplated herein. Ions contemplated herein can include, but are not limited to, zinc, magnesium, iron, calcium, CH3CO2, acetate, IO3, iodate, NH4, ammonium, iodide, N3, azide, lithium, barium Mg2+ magnesium, beryllium, manganate, HCO3, bicarbonate, hydrogencarbonate, mercuric mercury (II), HSO4, bisulfate hydrogen sulfate Hg2, mercurous mercury (I), HSO3, bisulfite hydrogen sulfite, metaborate, borate orthoborate, nitrate, bromate, nitrite, bromide, oxalate, calcium, oxide, carbonate, perbromate, -chlorate, perchlorate, chloride, periodate, chlorite, permanganate, chromate, peroxide, cupric, copper (II), 3-phosphate orthophosphate, cuprous copper (I), 3-phosphate, metaphosphate, cyanate, plumbic lead (IV), cyanide, plumbous lead (II), 2-dichromate K+ potassium, dihydrogen phosphate, silicate, ferric iron (III), sodium, ferrous iron (II), stannic tin (IV), fluoride, stannous tin (II), formate, sulfate, hydride, sulfide, hydrogen phosphate, sulfite, hydroxide, superoxide, hypobromite, thiocyanate, hypochlorite, thiosulfate and a combination thereof.

In some embodiments, bacillus spores, botox spores, anthrax spores, Shiga toxin (protein), Botox toxins (different types), Ms-2 bacterial, Ovalbumin, (protein) *Yersinia pestis* (vaccine), *Rickettsia* (antigen), VEE (Venezuelan Equine Encephalitis), Vaccinia viruses or a combination of organisms and organism byproducts are contemplated for generation of aptamers.

In other embodiments a aptamer can be selected to bind small organic molecules that include, but are not limited to, small, organic ligands, amino acids, nucleotides and derivatives, biological cofactors, antibiotics or other small molecules. In accordance with these embodiments, small molecules can include, but are not limited to, one or more of the following, organic dyes, Theophyllin, 1EHT, Dopamine, Hoechst 33258, sulforhodamine B, Sulforhodamine B, Cellobiose, D-tryptophan, L-arginine, L-citrullin, L-argininamide, L-arginine, L-arginine Mirror-image, L-valine, L-isoleucine, AMP, AMP Mirror-image, Guanosine, FMN, NAD, Vitamin B12, 8-oxo-dG, 5'-cap, Xanthene, Kanamycin A, Lividomycin, Tobramycin, Neomycin B, Viomycin, Chloramphenicol, Streptomycin, Rev peptide, Vasopressin Mirror-image and a combination thereof.

As one skilled in the art will readily appreciate, any method, technique or device capable of such detection and identification would have numerous medical, industrial and military applications. For instance, such methods, techniques and devices could be employed in the diagnosis and treatment of disease, to develop new compounds for pharmaceutical, medical or industrial purposes, or to identify chemical and biological warfare agents on a military facility or out in the field.

DCEs or RNA capture elements or aptamers contemplated herein may be used as tools in a variety of ways. For example, certain embodiments contemplated herein disclose using DCEs to recognize target agents as multianalyte, biosensing or metabolite profiling agents. DCEs can be immobilized on a suitable surface, such as an array or more particularly a microarray format. One advantage for using a microarray format is the ability to examine thousands of molecules in a sample, simultaneously. Typical methods used to immobilize single stranded DNA are based on covalent, affinity or electrostatic interactions between the DCE and a suitable surface. However, unlike standard DNA arrays, which may rely on multiple selection processes and amplifications to produce the DCE, DCEs that can be rapidly identified, isolated and amplified for use in a microarray format.

Uses

In some embodiments herein, DCEs or RNA aptamers may be generated for use in diagnosis for presence of a target agent, such as infectious and non-infectious disease and disease processes. In accordance with these embodiments, one or more DCEs may involve methods disclosed herein to generate DCEs against the whole infectious or non-infectious agent or a component or metabolite of the infectious agent or non-infectious agent or biomarker molecules induced during the course of infection with such an agent. In one example, DCEs directed against a component of the infectious agent or biomarker molecules induced during the course of infection may include DCEs generated against proteins; biomolecules altered by a metabolic disease or altered gene; or to measure levels (quantitative DCE assays) of a given biomolecule indicating a disease state (e.g. Alzheimers Disease progression, cancer progression, infection progression). It is contemplated herein that DCEs may be produced for diagnostic arrays, portable and/or handheld diagnostic devices, portable kits, or as therapeutic agents to control, revert, or eliminate the disorder or disorder progression.

Some advantages herein include advantages over some current technologies. One advantage of compositions, methods and systems disclosed herein include rare binding sequences (e.g. for generating rare DCEs) in the early stages of selection are preserved (versus eliminated by other technologies) and can be amplified. In addition, methods and systems disclosed herein can allow for the selection and amplification of all binding sequences from the very first round of selection. This can eliminate the need for subsequent rounds of selection. Once an aptamer, capture element, for example, a DCE is identified, isolated, and optionally amplified, and sequenced, these DCEs may be subjected to a more rigorous selection process under more stringent conditions of binding. In accordance with these embodiments, DCEs with the highest affinity, avidity and greatest specificity can be separately or simultaneously selected. In addition, the processes outlined above allow for reconstitution of a mixture if necessary to facilitate detection, identification and neutralization of the respective agent. Another advantage of these processes might be that part or all of these processes may be performed in a liquid flow system (modified flow cytometer or particle counter/sorter) which uses is adapted to use magnetic selection and in situ PCR for amplification of the sequences without further separation.

In other embodiments, using a modified existing flow cytometer, particle counter or sorter, one could use a hand held magnetic aptamer or DCE-quantum dot reader. The captured magnetic tagged DCE agent could be removed from the capture cassette of the reader and amplified directly in a thermal cycler. The free DCE produced in the supernatant could then be cloned and sequenced. This allows for the development of new DCEs against new agents very close to the field discovery, when random or pathogenic motif (modeled) DCE sequences or aptamers with random PCR primers are included in the set of known agent for handheld device field and/or portable use.

SELEX

One method for selection of DCE specificity involves the SELEX (Systematic Evolution of Ligands by EXponential enrichment) process. The SELEX process is well known in the art.

The SELEX method involves repeat selection from a mixture of candidate DCEs and step-wise iterations of binding, partitioning and amplification, using the same general selection scheme. Starting from a mixture of DCEs, preferably comprising a segment of randomized sequence, the method includes the following steps. Contacting the mixture with the target under conditions favorable for binding. Partitioning unbound DCEs from those DCEs that have bound specifically to target analyte. Dissociating the DCE-analyte complexes. Amplifying the DCEs dissociated from the DCE-analyte complexes to yield mixture of DCEs that preferentially bind to the analyte. But most labor intensive is reiterating the steps of binding, partitioning, dissociating and amplifying through many cycles in order to yield highly specific, DCEs that bind with high affinity to the target analyte.

By repeating the partitioning and amplifying steps, each round of candidate mixture contains fewer and fewer weakly binding sequences but also fewer rare binding sequences. The average degree of affinity of the DCEs to the target is suppose to increase with each cycle. The average number of selection rounds is around 4 to 11. Once the selection process is complete, then these sequences can be amplified.

This process can be automated by the use of a robot(s) to replace the human operator, but the process remains essentially the same and still as cumbersome. It also selects for the most probable binding aptamers (first), as well as, the most stringently bound (after the first few rounds, where rare sequences are overcome by the statistics of the PCR amplification process). This is one disadvantage and limitation of the current process for the selection of aptamers.

Quantum Dots

Embodiments herein utilize a selection process that is faster and more efficient than current technologies. In some embodiments, quantum dots are used to select DNA aptamers directed to bind a target agent optionally followed by amplification. Quantum dots, such as colloidal semiconductor nanocrystals, are sometimes as small as 2 to 10 nanometers. Self-assembled quantum dots are typically between 10 and 50 nanometers in size. At 10 nanometers in diameter, nearly 3 million quantum dots could be lined up end to end and fit within the width of a human thumb.

Quantum dots containing electrons can also be compared to atoms: both have a discrete energy spectrum and a small number of electrons. In addition, the confined electrons do not move in free space, but in the semiconductor host crystal. The quantum dot host material, in particular its band structure, playing an important role for all quantum dot properties. Typical energy scales, for example, are around 1 millielectron volt in quantum dots. It is relatively easy to connect quantum dots by tunnel barriers to conducting leads, which allows the application of the techniques of tunneling spectroscopy for their investigation.

In certain embodiments contemplated herein, luminescent colloidal semiconductor nanocrystals (e.g. quantum dots, qdot) that are inorganic fluorophores are used in methods disclosed herein to circumvent some of the functional limitations encountered by organic dyes. In particular, CdSe—ZnS core-shell qdot exhibit size-dependent tunable photoluminescence (PL) with narrow emission bandwidths (FWHM ~30 to 45 nm) that span the visible spectrum and broad absorption bands. Use of these nanocrystals allows simultaneous excitation of several particle sizes (colors) at a common wavelength. Therefore, simultaneous resolution of several colors using standard instrumentation can be performed. CdSe—ZnS qdot also have high quantum yields, are resistant to photodegradation, and can be detected optically at concentrations comparable to organic dyes.

Quantum dots have high energy levels and can be probed by optical spectroscopy techniques. In quantum dots that confine electrons and holes, the interband absorption edge is blue shifted due to the confinement compared to the bulk material of the host semiconductor material. As a consequence or selection benefit, quantum dots of the same material, but with different sizes, can emit light of different colors. Quantum dots have distinct optical applications due to their theoretically high quantum yield. In some embodiments, quantum dots of different size may be used to select different capture elements or aptamers contemplated of use in methods herein.

One of the optical features of small excitonic quantum dots is coloration recognizable to the naked eye. The major contributing factor of a qdot coloration is the size of the qdot. The larger the dot, the redder (the more towards the red end of the spectrum) the fluorescence; the smaller the dot, the bluer (the more towards the blue end). The coloration is directly related to the energy levels of the quantum dot. Larger qdots have more energy levels, more closely spaced, allowing the quantum dot to absorb photons containing less energy such as the ones closer to the red end of the spectrum. In addition, the shape of the qdot has also been implicated in the color spectrum. Embodiments contemplated herein include the use of several shapes and sizes of quantum dots, as well as selection of a size of dot based on the color emitted. It is appreciated that the selection of quantum dot of use in any of the compositions or methods herein can be optimized depending on the requirements of the particular use.

The ability to tune the size of quantum dots is advantageous, as the larger and more red-shifted the quantum dots, the less the quantum properties are variable. The small size of the quantum dot allows people to take advantage of these quantum properties.

Generation of Qdots

Some qdots are small regions of one material buried in another with a larger band gap. These can be so-called core-shell structures, e.g., with CdSe in the core and ZnS in the shell. Quantum dots sometimes occur spontaneously. Self-assembled quantum dots nucleate spontaneously under certain conditions during molecular beam epitaxy (MBE) and metallorganic vapor phase epitaxy (MOVPE), when a material is grown on a substrate to which it is not lattice matched. There are limitations of this method in cost of fabrication and lack of control over positioning of individual dots. Individual quantum dots can be created from two-dimensional electron or hole gases present in remotely doped quantum wells or semiconductor heterostructures. The sample surface is coated with a thin layer of resist. A lateral pattern is then defined in the resist by electron beam lithography. This pattern can then be transferred to the electron or hole gas by etching, or by depositing metal electrodes (lift-off process) that allow the application of external voltages between the electron gas and the electrodes.

Mass Production

In large numbers, qdots may be synthesized by means such as colloidal synthesis. Colloidal synthesis is a relatively cheap and has the advantage of being able to occur at benchtop conditions. This is one of the least toxic of all the different forms of synthesis.

Highly ordered arrays of qdots may also be self assembled by electrochemical techniques. Another method is pyrolytic synthesis, which produces large numbers of quantum dots that self-assemble into preferential crystal sizes. In modern biological analysis, various kinds of organic dyes are used. However, with each passing year, more flexibility is being required of these dyes, and the traditional dyes are simply unable to meet the necessary standards at times. Qdots have several advantages over traditional organic dyes, the brightness of high quantum yield as well as their stability having less photo destruction.

In addition, it is believed that it will be possible to achieve emission of white light via electrical stimulation as well as photonic of qdots, for other biological uses and detection methods contemplated herein. Quantum dots also require very little power since they are not color filtered.

Nucleic Acids

Nucleic acids within the scope may be made by any technique known to one of ordinary skill in the art. Examples of nucleic acids, particularly synthetic oligonucleotides, can include a nucleic acid made by in vitro chemical synthesis using phosphotriester, phosphite or phosphoramidite chemistry and solid phase techniques via deoxynucleoside H-phosphonate intermediates. In certain embodiments, DCEs or other aptamers contemplated herein can be generated and may be modified. Examples of modified DCEs include those that can be modified after amplification reactions such as PCR.™ or the synthesis of oligonucleotides. Examples of a biologically produced nucleic acids include recombinant nucleic acid production in living cells, such as recombinant DNA vector production in bacteria.

Nucleobase, nucleoside and nucleotide mimics or derivatives are well known in the art, and have been described. Purine and pyrimidine nucleobases encompass naturally occurring purines and pyrimidines and derivatives and mimics thereof. These include, but are not limited to, purines and pyrimidines substituted with one or more alkyl, carboxyalkyl, amino, hydroxyl, halogen (i.e. fluoro, chloro, bromo, or iodo), thiol, or alkylthiol groups. The alkyl substituents may comprise from about 1, 2, 3, 4, or 5, to about 6 carbon atoms.

Examples of purines and pyrimidines contemplated to modify DCEs produced herein can include, but are not limited to, deazapurines, 2,6-diaminopurine, 5-fluorouracil, xanthine, hypoxanthine, 8-bromoguanine, 8-chloroguanine, bromothymine, 8-aminoguanine, 8-hydroxyguanine, 8-methylguanine, 8-thioguanine, azaguanines, 2-aminopurine, 5-ethylcytosine, 5-methylcytosine, 5-bromouracil, 5-ethyluracil, 5-iodouracil, 5-chlorouracil, 5-propyluracil, thiouracil, 2-methyladenine, methylthioadenine, N,N-dimethyladenine, azaadenines, 8-bromoadenine, 8-hydroxyadenine, 6-hydroxyaminopurine, 6-thiopurine, 4-(6-aminohexyl/cytosine), and the like. In addition, purine and pyrimidine derivatives or mimics can be used as base substitutions in any of the methods disclosed herein. For example these can include, but are not limited to, 4-acetylcytidine, 5-methoxyaminomethyl-2-thiouridine, 5-(carboxyhydroxylmethyl)uridine, Beta,D-mannosylqueosine, 2'-O-methylcytidine, 5-methoxycarbonylmethyl-2 thiouridine, 5-carboxymethylaminomethyl, 5-methoxycarbonylmethyluridine, 5-carboxymethylaminomethyluridine, 5-methoxyuridine D Dihydrouridine, 2-methylthio-N-6-isopentenyladenosine, 2'-O-methylpseudouridine, N-((9-beta-D-ribofuranosyl-2 methylthiopurine-6-yl)carbamoyl)threonine, beta,D-galactosylqueosine, N-((9-beta-D-ribofuranosylpurine 6-yl)N-methyl-carbamoyl)threonine, 2'-O-methylguanosine, Uridine-5-oxyacetic acid methylester, Uridine-5-oxyacetic acid (v), N6-isopentenyladenosine, Wybutoxosine, 1-methyladenosine p Pseudouridine, 1-methylpseudouridine, Queosine, 1-methylguanosine, 2-thiocytidine m1I 1-methylinosine s2t 5-methyl-2-thiouridine m22g 2,2-dimethylguanosine, 2-thiouridine m2a 2-methyladenosine, 4-thiouridine, 2-methylguanosine, 5-methyluridine, 3-methylcytidine, N-((9-beta-D-ribofuranosylpurine 6-yl)carbamoyl)threonine, 5-methylcytidine, 2'-O-methyl-5-methyluridine, N6-methyladenosine, 2'-O-methyluridine, 7-methylguanosine, Wybutosine, 5-methylaminomethyluridine, 3-(3-amino-3-carboxypropyl)uridine, and combination thereof.

Amplification

In certain embodiments, the nucleic acids of the recognition complex system, DCEs, and/or RNA aptamers may be amplified to provide a source of high affinity nucleic acids for associating analytes. Amplification may also be of use in the iterative process for generating arrays with greater specificity or binding affinity for a target agent. Within the scope, amplification may be accomplished by any means known in the art. Exemplary embodiments are described herein.

Primers

The term primer, as defined herein, is meant to encompass any nucleic acid that is capable of priming the synthesis of a nascent nucleic acid in a template-dependent process. Typically, primers are oligonucleotides around 5-100 base pairs in length, but longer sequences may be employed. Primers may be provided in double-stranded or single-stranded form.

In some embodiments, amplification of a random region is produced by mixing equimolar amounts of each nitrogenous base (A, C, G, and T) at each position to create a large number of permutations (e.g. where "n" is the oligo chain length) in a very short segment. This provides dramatically more possibilities to find high affinity nucleic acid sequences when compared to the $10^9$ to $10^{11}$ variants of murine antibodies produced by a single mouse.

A number of template dependent processes are available to amplify the marker sequences present in a given template sample. One of the best known amplification methods is the polymerase chain reaction (referred to as PCR) which is described in detail in U.S. Pat. Nos. 4,683,195, 4,683,202 and 4,800,159, incorporated herein by reference in their entirety.

In other embodiments, other methods for amplification of nucleic acids, include but are not limited to, the ligase chain reaction ("LCR"), Qbeta Replicase, isothermal amplification methods, and Strand Displacement Amplification (SDA) as well as other methods known in the art. Still other amplification methods may be used in accordance with embodiments disclosed herein. Other nucleic acid amplification procedures may include transcription-based amplification systems (TAS), including nucleic acid sequence based amplification (NASBA). In some of the disclosed methods, the nucleic acid sequences may be prepared for amplification by standard phenol/chloroform extraction, heat denaturation of a clinical sample, treatment with lysis buffer and mini-spin columns for isolation of DNA and RNA or guanidinium chloride extraction of RNA. These amplification techniques involve annealing a primer which has DCE specific sequences. Following polymerization, DNA/RNA hybrids are digested with RNase H while double stranded DNA molecules are heat denatured again. In either case the single stranded-DNA is made fully double stranded by addition of second DCE specific primer, followed by polymerization. The double-stranded DNA molecules are then multiply transcribed by a polymerase such as T7 or SP6. In an isothermal cyclic reaction, the RNA's are reverse transcribed into double stranded DNA, and transcribed once against with a polymerase such as T7 or SP6. The resulting products, whether truncated or complete, indicate DCE specific sequences.

Polymerases and Reverse Transcriptases include but are not limited to thermostable DNA Polymerases: OnmiBase™. Sequencing Enzyme Pfu DNA Polymerase Taq DNA Polymerase Taq DNA Polymerase, Sequencing Grade TaqBead™ Hot Start Polymerase AmpliTaq Gold Tfl DNA Polymerase Tli DNA Polymerase Tth DNA Polymerase DNA POLYMERASES: DNA Polymerase I, Klenow Fragment, Exonuclease Minus DNA Polymerase I DNA Polymerase I Large (Klenow) Fragment Terminal Deoxynucleotidyl Transferase T4 DNA Polymerase Reverse Transcriptases: AMV Reverse Transcriptase M-MLV Reverse Transcriptase For certain embodiments, it may be desirable to incorporate a label into the nucleic acid sequences such as the DCEs, amplification products, probes or primers. A number of different labels can be used, including but not limited to fluorophores, chromophores, radio-isotopes, enzymatic tags, antibodies, chemiluminescent, electroluminescent, and affinity labels. In some embodiments, a label can be bound to a DCE to form a DCE probe. In accordance with this embodiment, the DCE probe can be used to detect a target agent in a sample. In one example, the DCE probe, capable of binding to at least a portion of a target agent, can be attached to a solid substrate (e.g. a microchip) and a sample suspected of having the target agent can be introduced to the solid substrate. Then, the solid substrate can be analyzed for formation of a complex of at least a portion of a target agent bound to the DCE. Presence of the complex is indicative that the target agent is present in the sample.

Examples of affinity labels contemplated herein, can include, but are not limited to, an antibody, an antibody fragment, a receptor protein, a hormone, biotin, DNP, and any polypeptide/protein molecule that binds to an affinity label.

Examples of enzymatic tags include, but are not limited to, urease, alkaline phosphatase or peroxidase. Colorimetric indicator substrates can be employed with such enzymes to provide a detection means visible to the human eye or spectrophotometrically visible.

The following fluorophores disclosed herein include, but are not limited to, Alexa 350, Alexa 430, AMCA, BODIPY 630/650, BODIPY 650/665, BODIPY-FL, BODIPY-R6G, BODIPY-TMR, BODIPY-TRX, Cascade Blue, Cy2, Cy3, Cy5,6-FAM, Fluorescein, HEX, 6-JOE, Oregon Green 488, Oregon Green 500, Oregon Green 514, Pacific Blue, REG, Rhodamine Green, Rhodamine Red, ROX, TAMRA, TET, Tetramethylrhodamine, and Texas Red.

Methods of Strand Separation

In some embodiments herein, double-stranded DNA (ds-DNA) sequences are separated into single stranded sequences for example, when single-stranded molecules are separated based on ability to recognize and bind a target agent. In accordance with these embodiments, the strands can be separated by any means known in the art including but not limited to melting by heat, cutting by DNAse, separating by non-specific chemical or physical action or binding of a ligand to which the aptamer or DCE is made specifically directed to associate. As used herein, the nanocrystal fluorescence (qdot) is de-quenched and observable by a fluorescent reader (e.g. a fluorometer). In one embodiment, a dequenched molecule indicates the binding of a specific target agent and separation of a reporter agent and a signal reducing agent. In some particular embodiments, strand separation and subsequent isolation indicates that an aptamer, DCE or RNA capture element is prepared for amplification. In certain embodiments, the single-stranded sequence regions may be amplified by an amplification technique such as polymerase chain reaction (PCR) for cloning, replication and sequencing to determine the sequences of the aptamers.

Solid Phase

It is contemplated herein that any solid phase support may be used for isolation or immobilization of a separated single stranded DNA capture element sequence (ssDCE) of any of the procedures disclosed herein. In some embodiments, a solid phase component can include beads or a bead technology for example beads, microbeads, particles, microparticles, nanoparticles or combination thereof. In accordance with these embodiments, the beads or particles may be selected from the group consisting of paramagnetic beads, magnetic beads, superparamagnetic beads, streptavidin coated beads, Reverse Phase magnetic beads, carboxy terminated beads, hydrazine terminated beads, Silica (sodium silica) beads and IDA (iminodiacetic acid) modified beads, aldehyde modified beads, Epoxy activated beads, DADPA-modified beads (beads with primary amine surface group), amino-polystyrene particles, carboxyl-polystyrene particles, Epoxy-polystyrene particles, dimethylamino-polystyrene particles, hydroxy-polystyrene particles, colored particles, flow cytometry particles, sulfonate-polystyrene particles or combination thereof.

Methods of Immobilization of Amplified Aptamers, Capture Elements and/or DCEs

In various embodiments, the amplified population of aptamers may be attached to a solid surface ("immobilized"). In one embodiment, immobilization may occur by attachment of an organic semiconductor to a solid surface, such as a magnetic bead, a plastic microtiter plate or a glass slide or a chip material. In one example, use of a semiconductor for this system is advantageous in that the attachment of aptamers may be readily reversed by addition of a chelator, such as EDTA if the attachment is through magnesium or some other chelatable compound.

Immobilization of aptamers may alternatively be achieved by a variety of methods involving either non-covalent or covalent interactions between the immobilized aptamers, comprising an anchorable moiety, and an anchor. In an exemplary embodiment, immobilization may be achieved by coating a solid surface with streptavidin or avidin and the subsequent attachment of a biotinylated polynucleotide. Immobilization may also occur by coating a polystyrene or glass solid surface with poly-L-Lys or poly L-Lys, Phe, followed by covalent attachment of either amino- or sulfhydryl-modified polynucleotides, using bifunctional crosslinking reagents by methods known in the art.

Other solid surfaces contemplated of use may include, but are not limited to, glass, plastic, silicon-coated substrate, macromolecule-coated substrate, particles, beads, microparticles, microbeads, dipstick, magnetic beads, paramagnetic beads and a combination thereof. In certain embodiments, these solid surfaces can be used to immobilize an amplified DCE for further use such as detecting an analyte or agent in a sample.

Immobilization may take place by direct covalent attachment of short, 5'-phosphorylated primers to chemically modified polystyrene plates. The covalent bond between the modified oligonucleotide and the solid phase surface is formed by condensation with a water-soluble carbodiimide. This method facilitates a predominantly 5'-attachment of the oligonucleotides via their 5'-phosphates. In addition, attachment to a solid surface may be made through non-covalently immobilizing aptamer molecules in the presence of a salt or cationic detergent on a hydrophilic polystyrene solid support containing an —OH, —C═O or —COOH hydrophilic group or on a glass solid support. The support is contacted with a solution having a pH of about 6 to about 8 containing the aptamer and the cationic detergent or salt. The support containing the immobilized aptamer may be washed with an aqueous solution containing a non-ionic detergent without removing the attached molecules.

One commercially available method for immobilization is the "Reacti-Bind.™. DNA Coating Solutions" (see Instructions—Reacti-Bind.™ DNA Coating Solution). This product comprises a solution that is mixed with DNA and applied to surfaces such as polystyrene or polypropylene. After overnight incubation, the solution is removed, the surface washed with buffer and dried, after which it is ready for hybridization. It is envisioned that similar products, i.e. Costar "DNA-BIND.™" or Immobilon-AV Affinity Membrane (IAV, Millipore, Bedford, Mass.) may be used in the practice of the embodiments disclosed herein.

Separation and Quantitation Methods

In some embodiments, it may be desirable to separate DCEs or RNA capture elements or other aptamers of different lengths for the purpose of quantitation, analysis or purification. In other embodiments it may be desirable to separate aptamers and group them by size in order to use them for methods disclosed herein.

Gel Electrophoresis

In one embodiment, amplification products can be separated by agarose, agarose-acrylamide or polyacrylamide gel electrophoresis using standard methods known in the art.

Separation by electrophoresis is based upon methods known in the art. Samples separated in this manner may be visualized by staining and quantitated, in relative terms, using densitometers which continuously monitor the photometric density of the resulting stain. The electrolyte may be continuous (a single buffer) or discontinuous, where a sample is stacked by means of a buffer discontinuity, before it enters the running gel/running buffer.

Chromatographic Techniques

Alternatively, chromatographic techniques may be employed to effect separation. There are many kinds of chromatography which may be used for example: adsorption, partition, ion-exchange and molecular sieve, and many specialized techniques for using them including column, paper, thin-layer and gas chromatography.

Microfluidic Techniques

Microfluidic techniques include separation on a platform such as microcapillaries, designed by ACLARA BioSciences Inc., or the LabChip.™ liquid integrated circuits made by Caliper Technologies Inc. These microfluidic platforms require only nanoliter volumes of sample, in contrast to the microliter volumes required by other separation technologies. Miniaturizing some of the processes involves genetic analysis has been achieved using microfluidic techniques known in the art.

Capillary Electrophoresis

In some embodiments, it may be desirable to provide an additional, or alternative means for analyzing aptamers. In these embodiment, microcapillary arrays are contemplated to be used for the analysis. These methods are well known in the art.

Aptamers Combinational Uses

Aptamers may be prepared by any method disclosed herein. In addition, aptamers may be used alone or in combination with other aptamers specific for the same target. Further, aptamers may specifically include "secondary aptamers" where a consensus sequence is derived from comparing two or more isolated aptamers that bind to a given target.

In general, a minimum of approximately 3 nucleotides, preferably at least 5 nucleotides, can effect specific binding. The binding specificity of the target/agent capture element complexes disclosed herein concern sufficient sequence to be distinctive in the binding aptamers and sufficient binding capacity of the target substance to obtain the necessary interaction. Oligonucleotides of sequences shorter than 10 bases can be feasible if the appropriate interaction can be obtained in the context of the environment in which the target is placed. Although some embodiments herein describe aptamers as single-stranded or double-stranded, it is contemplated that aptamers may sometimes assume triple-stranded or quadruple-stranded structures.

Any DCE or RNA capture element contemplated herein can contain a sequence that confers binding specificity, but may be extended with flanking regions and otherwise derivatized. In one particular embodiment, DCE binding sites will be flanked by known, amplifiable sequences, facilitating the amplification of the DCEs by PCR or other amplification techniques. In a further embodiment, the flanking sequence may comprise a specific sequence that preferentially recognizes or binds a moiety to enhance the immobilization of DCE to a substrate.

The DCEs found to bind to the targets may be isolated, sequenced, and/or amplified or synthesized as conventional DNA or RNA molecules. Alternatively, DCEs of interest may comprise modified oligomers. Any of the hydroxyl groups ordinarily present in DCEs may be replaced by phosphonate groups, phosphate groups, protected by a standard protecting group, or activated to prepare additional linkages to other nucleotides, or may be conjugated to solid supports. The 5' terminal OH is conventionally free but may be phosphorylated. Hydroxyl group substituents at the 3' terminus may also be phosphorylated. The hydroxyls may be derivatized by standard protecting groups. One or more phosphodiester linkages may be replaced by alternative linking groups. These alternative linking groups include, exemplary embodiments wherein P(O)O is replaced by P(O)S, P(O)NR.sub.2, P(O)R, P(O)OR', CO, or CNR.sub.2, wherein R is H or alkyl (1-20C) and R' is alkyl (1-20C); in addition, this group may be attached to adjacent nucleotides through O or S. Not all linkages in an oligomer need to be identical.

The DCEs generated or used as starting materials in a process may be single-stranded or double-stranded DNA. In a particular embodiment, the sequences are double-stranded DNA. The use of DNA eliminates the need for conversion of RNA aptamers to DNA by reverse transcriptase prior to PCR amplification. Furthermore, DNA is less susceptible to nuclease degradation than RNA. In preferred embodiments, the starting DCE will contain a randomized sequence portion, generally including from about 10 to 400 nucleotides, more preferably 20 to 100 nucleotides. The randomized sequence can be flanked by primer sequences that permit the amplification of DCEs found to bind to the analyte. The flanking sequences may also contain other convenient features, such as restriction sites. These primer hybridization regions can contain for example 10 to 80, or 15 to 40, or 20 to 40, bases of known sequence.

Both the randomized portion and the primer hybridization regions of the initial oligomer population are preferably constructed using conventional solid phase techniques. Such techniques are well known in the art. DCEs may also be synthesized using solution phase methods such as triester synthesis, known in the art. For synthesis of the randomized regions, mixtures of nucleotides at the positions where randomization is desired are added during synthesis.

Any degree of randomization may be employed. Some positions may be randomized by mixtures of only two or three bases rather than the conventional four. Randomized positions may alternate with those which have been specified. Indeed, it is helpful if some portions of the candidate randomized sequence are in fact known.

Nucleic Acid Chips, Aptamer Chips and Capture Element Arrays

Nucleic acid chips and capture element array technology provide a means of rapidly screening for target agents or samples suspected of containing a target agent for their ability to hybridize to a potentially large number of single-stranded capture element probes immobilized on a solid substrate. Contemplated herein are chip-based DNA technologies such as those known in the art. For example, these techniques involve quantitative methods for analyzing large numbers of samples rapidly and accurately. The technology capitalizes on the binding properties of single stranded DNA to screen samples. In some embodiments, DCE chips or arrays consists of a solid substrate upon which an array of single-stranded DCE molecules have been attached. A variety of DNA chip formats have been described in the art, for example U.S. Pat. Nos. 5,861,242 and 5,578,832 which are expressly incorporated herein by reference. In particular embodiments, a DCE may be tagged or labeled with a substance that emits a detectable signal, for example, a qdot or DALM.

Aptamers may be immobilized onto an integrated microchip that also supports a phototransducer and related detection circuitry. Alternatively, aptamers may be immobilized onto a membrane or filter which is then attached to the microchip or to the detector surface itself.

Exemplary substrates for immobilization of aptamers include, but are not limited to, nitrocellulose, nylon membrane or glass. Numerous other matrix materials may be used, including, but not limited to, reinforced nitrocellulose membrane, activated quartz, activated glass, polyvinylidene difluoride (PVDF) membrane, polystyrene substrates, polyacrylamide-based substrate, other polymers such as poly(vinyl chloride), poly(methyl methacrylate), poly(dimethyl siloxane) and photopolymers which contain photoreactive species such as nitrenes, carbenes and ketyl radicals capable of forming covalent links with target molecules.

It is contemplated herein that any of the aptamers used in compositions or methods can be one specific DCE or a mixture of aptamers directed to one or more target agent. Binding of aptamers to a selected support may be accomplished by any of several means known in the art. For example, DNA is commonly bound to glass by first silicanizing with for example, with amino or carboxy silane the glass surface, then activating with carbodiimide or glutaraldehyde.

Specific aptamers may first be immobilized onto a membrane and then attached to a membrane in contact with a transducer detection surface. This method avoids binding the aptamers onto the transducer and may be desirable for large-scale production. Membranes particularly suitable for this application include nitrocellulose membrane (e.g., from Bio-Rad, Hercules, Calif.) or polyvinylidene difluoride (PVDF) (BioRad, Hercules, Calif.) or nylon membrane (Zeta-Probe, BioRad) or polystyrene base substrates (DNA BIND Costar, Cambridge, Mass.).

CIE Analysis

Colorimetric analysis of a visible light signal (or signature) from an array of recognition complexes may be performed by CIE analysis. This refers to the standard curves for transformation of a spectral power distribution (SPD) into a set of three numbers that specifies a color, adopted in 1931 by the Commission Internationale de L'Eclairage (CIE). The CIE system determines how to convert an SPD into a set of three numerical components (tristimulus values) that are the equivalent of coordinates in 3-dimensional color space. By generating a unique set of coordinates from an array spectral emission, CIE analysis may be used to provide a "signature" for a target agent. These methods are known in the art. In addition, CIE colorimetry tables may be used for analysis. Determination of CIE values, analysis of data and the use of neural networks and lookup tables have been previously described.

EXAMPLES

The following examples are included to demonstrate some embodiments. It should be appreciated by those of skill in the art that the techniques disclosed in the examples which follow represent techniques discovered by the inventors to function well in the practice of embodiments disclosed herein, and thus can be considered to constitute exemplary modes for its practice. However, those of skill in the art should, in light of the present disclosure, appreciate that many changes can be made in certain embodiments which are disclosed and still obtain a like or similar result without departing from the spirit and scope herein.

DNA Based Recognition Complex System
Methods and Materials

In one exemplary method, arrays of DCEs were generated: 1) a naturally occurring overlapping random (N) 60 mer; and 2) a contiguous or ligated array. In the latter array, DCE diversity was increased, compared to the starting random 60mers, by truncating longer chains with the addition of dideoxynucleotides during a PCR step and covalently linking non-contiguous DNA chains together with Taq DNA ligase.

In one example, the PCR chain termination step involved addition of 6.6 µg of random (N) 60mer as a self-priming (due to partial hybridization) PCR template with 8 µg of each deoxy/dideoxynucleotide (e.g. d/ddA, d/ddC, d/ddG, d/ddT) and 20 µl (80 units) of Taq polymerase per tube. The tubes were PCR amplified using the following temperature profile: 96° C for 5 min, followed by 40 cycles of 96° C for 1 min, 25° C for 1 min, and 72° C for 1 min. PCR extension was completed at 72.degree. C. for 7 min and tubes were stored at 4 to 6° C until electrophoresed. The collection of DCE species present as overlapping random (N) 60mers or as ligated and truncated DNAs constituted a library of DCEs.

For both types of DNA arrays, 3.3 µg (typically 5 to 10 µl) of library DNA was diluted with 2x. loading buffer and loaded into each well of precast 10% or 4-20% gradient mini TBE polyacrylamide gels and electrophoresed in cold 1.times. TBE for 1 h at 100 V per gel. If DNA was to be visualized in the gel, gels were stained with 0.5 µg/ml ethidium bromide in TBE for 10 min, followed by rinsing in deionized water for 30 min and photography on a 300 nm ultraviolet transilluminator using Polaroid type 667 film.

Arrays of DCEs were generated from library DNA separated by electrophoresis (size and charge). Analyte binding and nucleic acid hybridization to the DCE arrays were assayed as follows:

Gels were cut into strips containing the one-dimensional DNA arrays of either type and were added to 10 ml of BB. Gel strips were allowed to equilibrate in their respective buffers for 10 min at room temperature (RT) with gentle shaking and were then scanned as described below prior to addition of analytes. All DNA analytes were added at a final concentration of 5 µg/ml and all protein analytes were added at a final concentration of 10 µg/ml in BB for 1 hr at RT with gentle shaking. Gels were gently rinsed twice in 10 ml of BB, carefully repositioned and rescanned on a luminescence spectrometer.

In one example, a Perkin-Elmer (Beaconsfield, Buckinghamshire, UK) model LS 50B luminescence spectrometer equipped with a plate reader was used in the thin layer chromatography (TLC) plate mode to scan DCE arrays in gel slices before and after addition of various analytes. After minor swelling or shrinkage in each of the reaction buffers, gel strips were generally 95 to 96 mm in length, with the DNA array being contained in the lower most 65 mm of each gel strip. Gel strips were scanned with an excitation of 260 nm (10 nm slits), emission of 420 nm (10 nm slits) and 1 mm resolution (i.e., scanned in 1 mm increments).

Example 1

In one exemplary method, DCEs against phospholipase A2 (venom) of Crotalus durissus terrificus, a South American Rattlesnake were generated.

Step 1: A primary strand of DNA (ss-DNA: random sequence or known sequence aptamers, such as BA, Shiga, and Tularemia aptamers), (e.g. SIGMA Genosys) is added to the amino polybeads (e.g. 108 nm, PolySciences, Inc, Product No. 16586-5) in 0.1 M MOPS buffer. EDC (1-Ethyl-3-(3-dimethylaminopropyl) carbodiimide HCL, PIERCE, Product No. 22981) and imidazole (EASTMAN Organic Chemicals, Product No 7433) are added with stirring. (e.g. Average number of primary strand DNA/bead=5.5) The reaction mixture is stirred at room temperature overnight. Product 1 from step 1 was separated by centrifuging and washed twice with H2O, then re-suspended in MOPS buffer.

Step 2: Excess complementary strand DNA was added to product 1 in 0.1M MOPS buffer. The mixture is stirred (or shaken) for 1 day at 60° C and overnight at room temperature. Product 2 from step 2 was separated by centrifuging and washed twice with H2O.

Step 3: Product 2 was re-suspended in a saturated solution of quencher such as QXL 610 (PH=10, excess QXL 610 used, ANASPEC, Inc. Product No. 81818), then EDC and imidazole are added. Reaction mixture is stirred overnight. Product 3 was separated by centrifuging and washed twice with H2O.

Step 4: Product 3 was re-suspended in 10 ml of reaction buffer (350 ul 2M Tri-HCl, 100 ul 1M MgCl2, and 7.7 mg DTT). Then 5 ml of ATP (27.6 mg ATP) and 2 ul of T4 Polynucleotide Kinase (USB Corporation) are added. Reaction mixture is shaken for 1-2 hr at 37° C. Product 4 was separated by centrifuging and washed twice with H2O.

Step 5: Product 4 was re-suspended in a solution of Quantum Dots in MOPS buffer (excess Q-Dots used, Evident Technologies, Product No. ET-C11-AM1-0600). EDC and imidazole are added. The mixture is stirred overnight. Product 5 was separated by centrifuging and washed twice with H2O.

Example 2

In one exemplary method, interaction and separation of DCEs (made from random DNA) with Phospholipase A2 (e.g. purchased from SIGMA) was performed using 5 different randomly sequenced DNA strands with differing GC/AT ratios. DCEs are made according to Example 1 discussed previously, (#1 GC/AT=43/27, #2 GC/AT=40/30, #3 GC/AT=38/32, #4 GC/AT=35/35, #5 GC/AT=30/40). Total length of random DNA is 70 bp plus 20 bp primer (both strands). Approximately, 6 ul of phospholipase A2 (5 ng/ul, Sigma, Product No. P5910) was added to a mixture of DCEs made from random DNA #1 to #5 in 0.1X PBS buffer. (50 ul of each DCE, 50 ul of DCE contains about $2\times10^{12}$ primary ss-DNA molecules).

Then the mixture was agitated for 10 minutes. Approximately, 30 μl of magnetic beads (Spherotech, Product No. AMS-40-10) attached to 60 bp random ss-DNA are added. (30 ul of magnetic beads contains about $1\times10^{11}$ ss-DNA molecules) The mixture is agitated for another 10 minutes. Magnetic beads attach to denatured DCEs and are then separated by magnet. Fluorescence of the magnetic beads indicates that not only denatured DCEs are pulled out; some un-denatured DCEs are pulled out (same amount of magnetic beads are used as control). The magnetic beads were washed 2-3 times with PBS buffer at room temperature and the fluorescence of washed magnetic beads indicates that un-denatured DCEs are washed away. The washed magnetic beads were vortexed for 10-15 min. and supernatant was separated by magnet attraction. Fluorescence of magnetic beads indicates that some denatured DCEs are still attached to the magnetic beads. The DNAs of the supernatant were then amplified by PCR, cloned and sequenced.

Data is shown in Table 1 and FIGS. 1 and 2.

TABLE 1

Fluorescent change from interaction and separation of DCEs (made from random DNA) with Phospholipase A2 (Fluorescent measurement are taken by Plate Reader, Synergy HT, SCIMTRICS)

| Time (min) | Before Washing Magnetic Beads Control | Magnetic beads Separated from Mixture of DCEs and agent by magnet | Difference of Fluorescence |
|---|---|---|---|
| 0 | 785 | 17038 | 16253 |
| 2 | 808 | 16806 | 15998 |
| 4 | 830 | 16954 | 16124 |
| 6 | 883 | 16846 | 15963 |
| Time (min) | Magnetic Beads Control | After Washing Magnetic beads Separated from Mixture of DCEs and agent by magnet | Difference of Fluorescence |
| 0 | 905 | 10331 | 9426 |
| 2 | 935 | 8620 | 7685 |
| 4 | 934 | 7981 | 7047 |
| 6 | 960 | 7767 | 6807 |
| Time (min) | Magnetic Beads Control | After vortex Magnetic beads Separated from Mixture of DCEs and agent by magnet | Difference of Fluorescence |
| 0 | 1025 | 4949 | 3924 |
| 2 | 1012 | 4479 | 3467 |
| 4 | 1015 | 4474 | 3459 |
| 6 | 1004 | 4563 | 3559 |

FIG. 4. Fluorescent change from interaction of individual DCEs (made from random DNA) with Phospholipase A2 (Fluorescence measurements are taken by Plate Reader, Synergy HT, SCIMTRICS) (13.6 ng phospholipase A2 are used for each sample)

PCR, cloning, and sequencing of DNA in the supernatant separated from interaction of DCE mixture with phospholipase A2 (see the procedures for DCE sequencing below).

Interaction and separation of DCEs (made from random DNA) with Phospholipase A2 has been repeated and same results are obtained. (Table 2 and FIGS. 6 and 7A-7C)

TABLE 2

Fluorescent change from interaction and separation of DCEs (made from random DNA) with Phospholipase A2 (Fluorescent measurement are taken by Plate Reader, Synergy HT, SCIMTRICS)

| Time (min) | Before Washing Magnetic Beads Control | Magnetic beads Separated from Mixture of DCEs and agent by magnet | Difference of Fluorescence |
|---|---|---|---|
| 0 | 813 | 9756 | 8943 |
| 2 | 780 | 8987 | 8207 |

TABLE 2-continued

Fluorescent change from interaction and separation of DCEs (made from random DNA) with Phospholipase A2 (Fluorescent measurement are taken by Plate Reader, Synergy HT, SCIMTRICS)

| | | | |
|---|---|---|---|
| 4 | 816 | 8186 | 7370 |
| 6 | 796 | 7528 | 6732 |

| Time (min) | Magnetic Beads Control | After Washing Magnetic beads Separated from Mixture of DCEs and agent by magnet | Difference of Fluorescence |
|---|---|---|---|
| 0 | 819 | 5547 | 4728 |
| 2 | 834 | 5128 | 4294 |
| 4 | 863 | 4817 | 3954 |
| 6 | 928 | 4600 | 3672 |

| Time (min) | Magnetic Beads Control | After Vortex Magnetic beads Separated from Mixture of DCEs and agent by magnet | Difference of Fluorescence |
|---|---|---|---|
| 0 | 1009 | 2435 | 1426 |
| 2 | 1008 | 2391 | 1383 |
| 4 | 1026 | 2334 | 1308 |
| 6 | 1025 | 2252 | 1227 |

Example 3

In another exemplary method, interaction and separation of DCEs (made from known aptamers) with agents was performed. Based the procedures mentioned above, DCEs with known aptamers for example BA, Shiga, and Tularemia have been made and interactions of BA spores and Tularemia agent with DCE mixture have been tried.

Step 1: Denatured aptamer separated by magnetic beads with random DNA (60 bp) after interacting of DCEs (made from BA, Shiga, and Tularemia aptamers) in one example, BA spores. The aptamer was amplified by PCR. Cloning, and sequencing of the aptamer illustrated sequence of this example, BA aptamer Step 2: In another example, Tularemia agent was used instead of the first example, BA spores, cloning and sequencing show sequence of Tularemia aptamer.

In one exemplary method a procedure for DCE amplification was demonstrated.

Step 1: Amplification: After boiling, the supernatant was separated from the washed magnetic beads. It was then divided into 12-5 μl samples for amplification through PCR. Master Mix (per 5 μl template sample) was as follows: 5 μl buffer, 2 μl MgCl, 2.5 μl DMSO, 1 μl betaine, 1 μl each dNTPs, 2.5 μl F primer, 2.5 μl R primer, 0.54 μl taq polymerase, 25.1 μl H2O. Betaine and increased DMSO were added to the master mix to eliminate polymerase jumping during PCR amplification.

Step 2: Dialysis: The 12 amplified samples were run on a 2.5% agarose gel, and the bands of interest were cut out. Slices were combined and placed into two dialysis bags containing 0.1X TAE. The bag was then immersed in a shallow layer of 1X TAE in an electrophoresis tank. Current (110V) was applied for approximately 20 minutes. Polarity was reversed for 1 minute. The buffer from the bag was then transferred to a disposable 2.0 ml centrifuge tube.

Step 3: Phenol/Chloroform extraction. After phenol/chloroform extraction resulting pellets were resuspended in 5 μl TE. 2 μl of each sample was run on a 2.5% agarose gel. Samples 1 and 2 were then combined into one centrifuge tube and labeled as Random.

Step 4: Ligation and Transformation. Using, for example, a TOPO TA Cloning® Kit (Invitrogen), 0.5 μl, 1.5 μl, and 3 μl of random DNA was ligated into the provided vector (pCR®II-TOPO®). To each ligation 1 ml SOC was added and incubated at 37° C with shaking (225 rpm) for 1 hour. Transformations were streaked to LB Amp plates and incubated overnight at 37° C.

Step 5: Boilprep and PCR check: Twelve Colonies were isolated on an Xgal/IPTG LB Amp plate and the three resulting white colonies underwent boil preparation with colony lysis buffer. Boil preparation supernatants were used in a PCR reaction to ensure ligation/transformation success.

Step 6: Sequencing: PCR precipitates (1 μl each) were sequenced with in one exemplary method, BigDye® Terminator RR chemistry (BigDye® Terminator v3.1 Sequencing Standard Kit, Applied Biosystems, Part No. 4336935) and run on a sequencer, Applied Biosystems 3100 automated sequencer. According to the fluorescence change data, DCE 2 (GC ratio 40) and DCE 5 (GC ratio 30) were expected to be found in sequencing.

```
Forward Primer:
                                        (SEQ ID NO: 1)
ACCCCTgCATCCTTTgCTgg Reverse Primer:
                                        (SEQ ID NO: 2)
AgTCTAgAgggCCCCAgAAT DCE 2 (GC ratio 40) primary strand:
                                        (SEQ ID NO: 3)
ACCCCTgCATCCTTTgCTgggCATgTCCgATgCgAACCggATCCAATgTC gATCAgCCggTTACCgCgCTAggTATgTCgATCgCTAggAAgTCTAgAgg gCCCCAgAAT DCE 2 (GC ratio 40) complimentary strand:
                                        (SEQ ID NO:4)
TggggACgTAggAAACgACCCgTACAggCTACgCTTggCCTAggTTACAg CTAgTCggCCAATggCgCgATCCATACAgCTAgCGATCCTTCAgATCTCC CggggTCTTA DCE 5 (GC ratio 30) primary strand:
                                        (SEQ ID NO: 5)
ACCCCTgCATCCTTTgCTgggATTAACGAGTAACTTTggggCggTTgAgT TCATggATTAAATCAAgTATgggTTTgCCgAAgTAgCCAAAgTCTAgAgg gCCCCAgAAT DCE 5 (GC ratio 30) complimentary strand
                                        (SEQ ID NO: 6)
TggggACgTAggAAACgACCCTAATTgCTCATTgAAACCCCgCCAACTCA AgTACCTAATTTAgTTCATACCCAAACggCTTCATCggTTTCAgATCTCC CggggTCTTA
```

In one exemplary embodiment, when a target molecule is introduced to the DCE mixture such as a toxin, it is contemplated that the target molecule may bind to the primary or complimentary strand or a combination thereof for any DCE in question. In this example, the amplified product is a double stranded product. This double stranded product can then be incorporated into the vector with either the primary strand on top or the complimentary strand on top. In this example, the reads were on average 400 bp in length.

The following nucleotides reads provided contain the relevant insert information.

Random Sequence 1

(SEQ ID NO: 7)
CCCTTATTCTggggCCCTCTAgACTTTggCTACTTCggMAAACTCATACT

TgATTTAATCCATgAACTCAACCgCCCCAAAgTTACTCgTTAAACCCCAg

CAAAggRTgCRggggWAAggg

The random sequence ligated to the vector and transformed was DCE 5 (GC ratio 30). The compliment strand is shown.

Random Sequence 2

(SEQ ID NO: 8)
CCCTTATTCTggggCCCTCTAgACTTTggCTACTTCMCCgCCCAAAgTTC

TCgTTACCCCAgCAAAggATgCAggggTAAggg

The random sequence ligated to the vector and transformed was DCE 5 (GC ratio 30). The compliment strand is shown.

Random Sequence 3

(SEQ ID NO: 9)
CCCTTACCCCTgCATCCTTTgCTgggCATgTCCgATgCgAACCggATCCA

ATgTCgATCAgCCggTTACCgCgCTAggTATgTCgATCgCTAggAAgTCT

AgAgggCCCCAgAATAAggg

The random sequence ligated to the vector and transformed was DCE 2 (GC ratio 40). The primary strand is shown.

Example 4

In one exemplary method, separations and sequencing of BA spores and tularemia agents with a mixture of DCEs (BA DCE, Shiga DCE, and Tularemia DCE) using a separation procedure were performed. Here, denatured DCE (or aptamer) were isolated by magnetic beads then amplified by PCR, cloned and sequenced. These experiments confirm that this improved method is generally applicable for generating specific DCEs to a particular target even when the target is presented in a composition. In FIG. 10, interaction, isolation, PCR, sequencing of BA spores with a mixture of BA DCE, Shiga DCE, and Tularemia DCE are demonstrated in a schematic diagram. FIG. 11 illustrates a graph representing fluorescent change resulting from interactions of BA DCE with BA spores, Shiga toxin, and Tularemia agent.

TABLE 3 represents relative fluorescence of a product separated from interaction of BA spores with a mixture of BA DCE, Shiga DCE, and Tularemia DCE

| Time(min) | Magnetic Beads with random DNA Control D6 | Magnetic Beads plus Sample After washing twice D7 | Diff. |
|---|---|---|---|
| 0 | 959 | 2588 | 1629 |
| 2 | 1008 | 2757 | 1749 |
| 4 | 955 | 2880 | 1925 |
| 6 | 988 | 2929 | 1941 |
| 8 | 982 | 2977 | 1995 |
| 10 | 955 | 2998 | 2043 |

Figure 12:
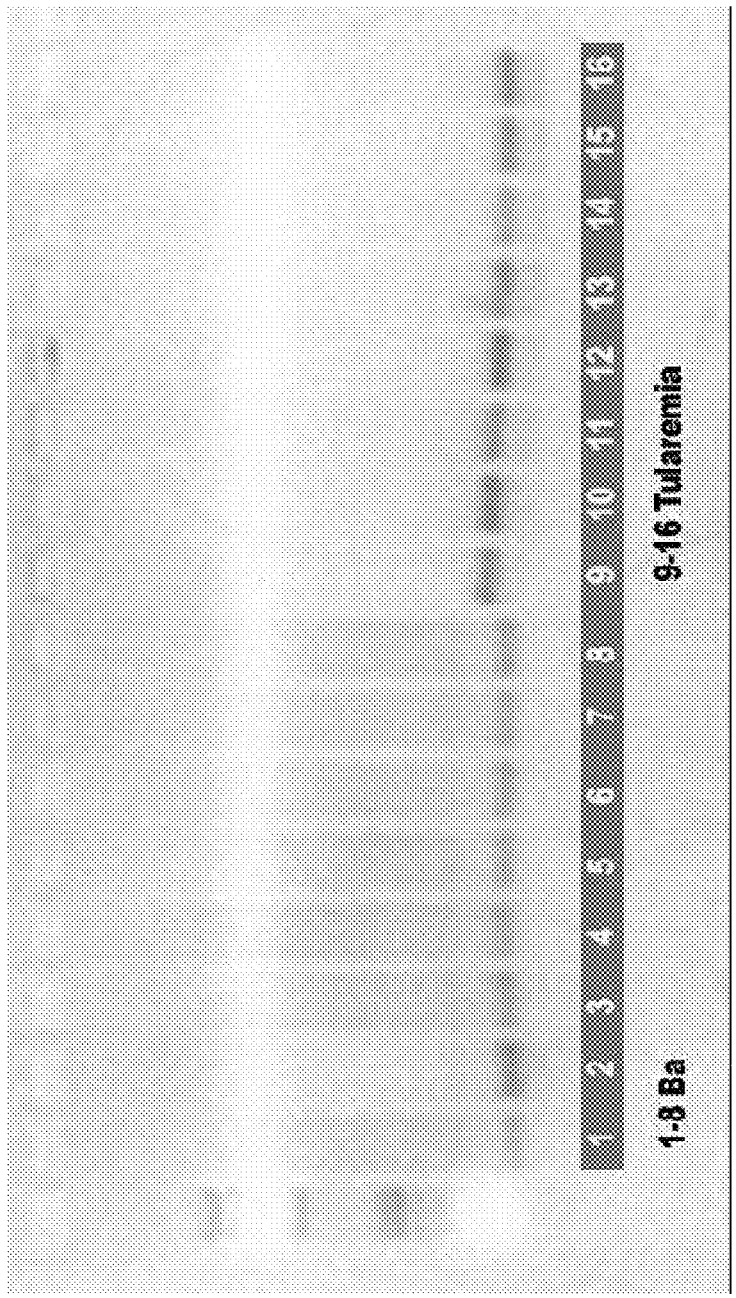
FIG. 12 represents an exemplary gel of PCR products produced from isolates of methods.

FIG. 12 represents a picture of an acrylamide gel demonstrating the PCR products produced by an exemplary method for generating DCEs herein. The PCR products isolated from interaction of BA spores with a mixture of BA DCE, Shiga DCE, and Tularemia DCE See attached PCR picture. The one labeled "initial" is straight from the sample isolated from reaction mixture. The first 8 samples are Ba and the next 8 are Tularemia (FTJ).

Sequence of one product isolated from interaction of BA spores with a mixture of BA DCE, Shiga DCE, and Tularemia DCE.

(SEQ ID NO: 10)
ACCCCTgCATCCTTTgCTggAgAggAATgTATAAggATGTTCCgggCgTg

TgggTAA^TCAgTCTAgAgggCCCCANAAT

The following sequence illustrates a DCE corresponding to a sequence of BA DCE (OAL-7)

(SEQ ID NO: 11)
ACCCCTgCATCCTTTgCTgg,AgAggAATgTATAAggATGTTCCgggCgT gTgggTAAgTC,AgTCT,AgAgggCCCCAgAAT

TABLE 4 represents fluorescence or product separated from interaction of Tularemia agent with a mixture of BA DCE, Shiga DCE, and Tularemia DCE.

| Time(min) | Magnetic Beads with random DNA Control H2 | Magnetic Beads Plus Sample After washing twice H6 | Diff. |
|---|---|---|---|
| 0 | 1084 | 2448 | 1364 |
| 2 | 1091 | 2662 | 1571 |
| 4 | 1063 | 2849 | 1786 |
| 6 | 1051 | 2963 | 1912 |
| 8 | 1082 | 3138 | 2056 |
| 10 | 1043 | 3227 | 2184 |

A sequence of a product isolated from interaction of tularemia agent with a mixture of BA DCE, Shiga DCE, and Tularemia DCE is SEQ ID NO: 12.

(SEQ ID NO: 12)
ACCCCTgCAggATCCTTTgCTggTACCACTACCTAACACCTACCTTCCCT

CCCATCgTCCgCTgCACAgAgTATCgCTAATCAgTCTAgAgggCCCCAgA

AT

SEQ ID NO: 13 represents a sequence of Tularemia aptamer (FTJ-22) isolated by the described method.

(SEQ ID NO: 13)
ACCCCTgCAggATCCTTTgCTggTACCACTACCTAACACCTACCTTCCCT

CCCATCgTCCgCTgCACAgAgTATCgCTAATCAgTCTAgAgggCCCCAgA

AT

Example 5

Figure 13:
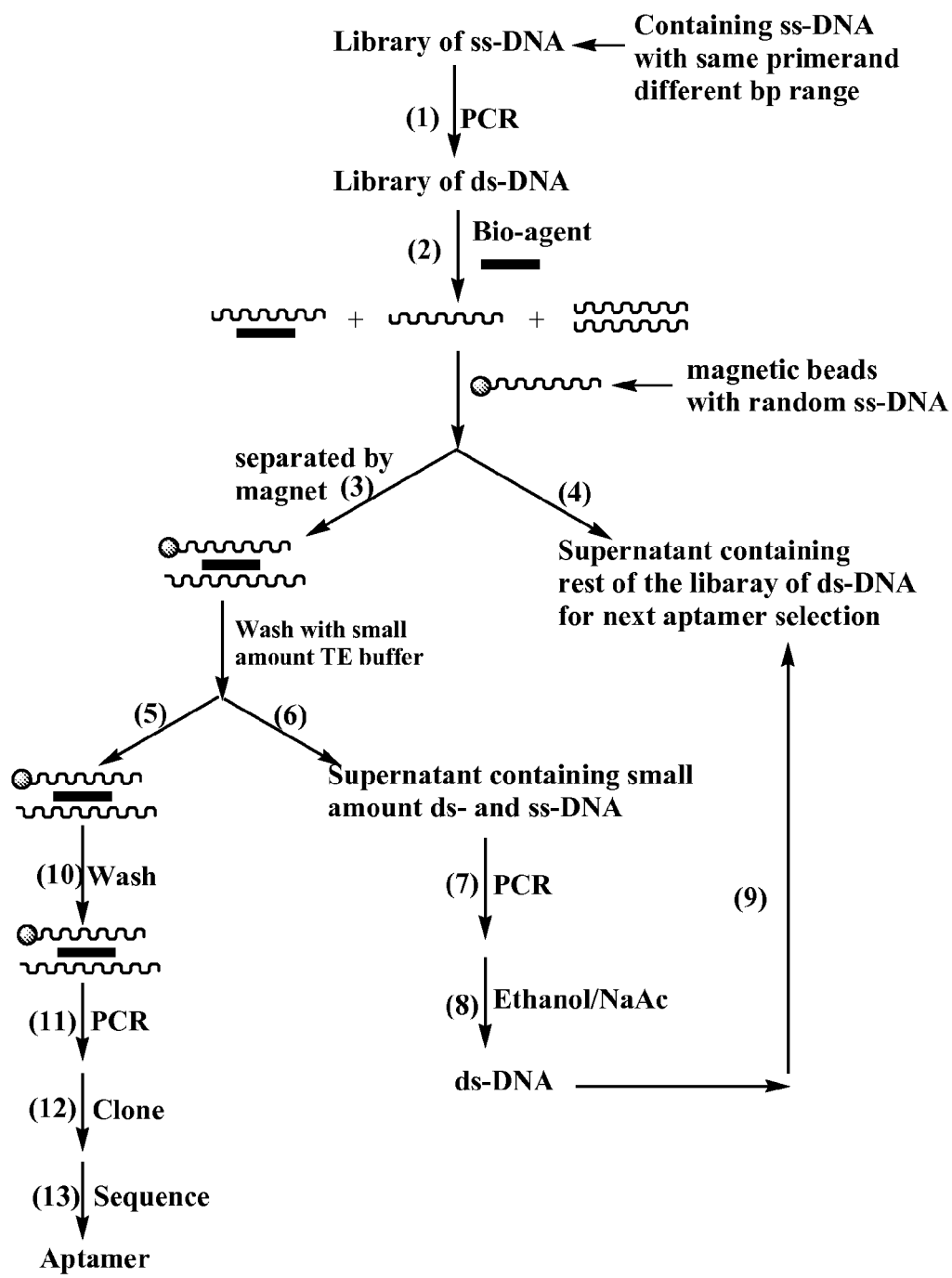
FIG. 13 represents a schematic of an exemplary processing procedure of rapid aptamer selection.

In one exemplary method (see Schematic FIG. 13), aptamers are generated to a target molecules as follows. For example, 1) ss-DNA is converted to ds-DNA. 2) Then a bioagent (target molecule) denatures the ds-DNA, binding to the ss-DNA with the strongest affinity for it. Magnetic beads are added. After addition of magnetic beads, the ss-DNA/bio-agent (target agent) complex can be separated by a magnet. Supernatant containing remaining library of ds-DNA can be separated from the reaction mixture and can be used for the next aptamer selection. Then the aptamer/bio-agent/magnetic bead complex (5) separated by magnet can be washed with a small amount buffer (e.g. Tris-EDTA buffer) and separated from the supernatant. The supernatant containing small amount of ss-DNA and ds-DNA is separated. The ss-DNA and ds-DNA in supernatant (6) are converted to ds-DNA. The ds-DNA from (7) can be purified by ethanol/NaAc precipitation. Purified ds-DNA can be mixed with the library of ds-DNA and ready for next aptamer selection. The aptamer/bio-agent/magnetic bead complex can be washed thoroughly with water. The aptamer of aptamer/bio-agent/magnetic bead complex can then be amplified by PCR or other suitable procedure. The amplified aptamers are cloned and then the aptamer can be sequenced.

Process of rapid aptamer selection: In one example, the procedure for rapid aptamer selection is shown FIG. 13. The starting libraries consisted of a multitude of ss-DNA fragments (~10$^{15}$ molecules) with a central random region of 30-, 40-, and 50-nucleotides, flanked by 20-nucleotide constant regions that function as primer binding sites for PCR. Before selection, each library of ss-DNA was amplified in parallel PCR reactions to produce a library of ds-DNA. After ethanol precipitation, each ds-DNA library was re-suspended in PBS buffer (1×, with Mg$^{+2}$ and Ca$^{+2}$) and mixed together. (Three libraries of ds-DNA were used here). A small amount of target was then added to the mixture of ds-DNA libraries and stirred for 0.5 hour (Here ~0.75 ng BoTox-type A or B; light chain was used). The target denatured the ds-DNA and bound to the ss-DNA (aptamer) with the strongest affinity for it. Then, magnetic beads connected to random ss-DNA (60mer) were added and interacted with the aptamer/target complex. This then became a complex of aptamer/target/magnetic beads which was separated by magnet. Supernatant containing the remaining library of ds-DNA was separated from the reaction mixture and used for the next aptamer selection. Then, the complex of aptamer/target/magnetic beads was washed with a small amount of TE buffer and separated from the supernatant. The small amount of ss-DNA and ds-DNA contained in the supernatant was amplified by PCR and converted to ds-DNA, then mixed with the library of ds-DNA for the next aptamer selection. The aptamer/target/magnetic bead complex was washed thoroughly with water. Then, the aptamer of the aptamer/target/magnetic bead complex was amplified by PCR, cloned, and sequenced.

Exemplary methods for selection, amplifying, cloning, and sequencing of BoTox aptamers (type A and B-light chain) by rapid selection methods disclosed herein ~0.75 ng of BoTox (type A or B-light chain) was added to the library of ds-DNA (70, 80, and 90mers). The mixture was stirred at room temperature for a half hour. Then, 30 µl of magnetic beads with random ss-DNA attached (~7.485×10$^6$ bead, ~1.16×10$^{12}$ ss-DNA) was added and stirred for another half hour. The complex of aptamer/target/magnetic bead was separated by magnet, washed thoroughly with water and re-suspended in TE buffer. The ss-DNA (aptamer) of the aptamer/target/magnetic bead complex was then amplified by PCR. The sample was first divided into 5 µl aliquots for amplification through PCR. Master Mix (per 5 µl template sample) was as follows: 5 µl buffer, 2 µl MgCl2, 2.5 µl DMSO, 1 µl betaine, 1 µl each dNTP, 2.5 µl F primer, 2.5 µl R primer, 0.54 µl taq polymerase, 25.1 µl H2O. Betaine and increased DMSO were added to the master mix to eliminate polymerase jumping during PCR amplification.10 Using TOPO TA Cloning® Kit 1 µl of amplified DNA was ligated into the provided vector (pCR®II-TOPO®). To each ligation, 1 ml SOC was added and incubated at 37° C with shaking (225 rpm) for 1 hour. Transformations were streaked to Xgal/IPTG LB Amp plates and incubated overnight at 37° C. Selected white and/or light blue colonies were isolated and grown O/N on LB amp plates. Colonies were then grown up overnight for miniprep. 5 µl from miniprep (precipitate in 30 µl TE buffer) was used as PCR template. Two colonies from each Xgal/IPTG LB Amp plate underwent boilprep with colony lysis buffer (1% Tween20 in Tris-EDTA). 15 µl was used as template in PCR. PCR products were precipitated with 5M ammonium acetate and 100% IPA at −20° C overnight. PCR precipitates (1 µl each) were sequenced with BigDye® Terminator RR chemistry (BigDye® Terminator v3.1 Sequencing Standard Kit, Applied Biosystems, Part No. 4336935) and run on an Applied Biosystems 3100 automated sequencer. Table 5 shows sequences of BoTox aptamers (Type A & B, light chain) selected by rapid selection methods disclose herein. Aptamers of BoTox toxins (type A & B-light chain), Ovalbumin, B$_a$. and B$_t$ spores, MS-2 bacteria have been selected through the techniques and methods disclosed herein. Only the sequences of two BoTox aptamers and their testing results are demonstrated herein. MS-2 bacteria have been selected through methods and systems disclosed herein. The sequences of two BoTox aptamers and their testing results are demonstrated here.

Selection, PCR, Cloning and Sequencing of BoTox Aptamers

Selection procedures of BoTox aptamers are described above. PCR, cloning, and sequencing are the same as those described. In certain embodiments, sequences of BoTox aptamers are used for one exemplary analysis Sequences of three aptamers for BoTox toxin (type A-light chain) are obtained (two of them are complimentary to each other) using methods disclosed herein.

TABLE 5

Sequences of BoTox aptamers selected by rapid selection processes disclosed herein.

| BoTox aptamers for type A-light chain |
|---|
| LCA 1(+). AgTCTAgAgggCCCCAgAATACACCCgACAACTAgATACCCATC AAAAgTCCAgCAAAggATgCAggggT, SEQ. ID NO: 14 |
| LCA 1(−). ACCCCTgCATCCTTTgCTggACTTTTgATgggTATCTAgTTgTC gggTgTATTCTggggCCCTCTAgACT, SEQ. ID NO: 15 |
| LCA 2. ACCCCTgCATCCTTTgCTgggCTATAgTTgTCAAAACACCTgTg ggATTgATTCTggggCCCTCTAgACT, SEQ ID NO: 16 |
| Botox aptamers for type B-light chain |
| LCB AgTCTAgAgggCCCCAgAATTATCCACTAgCgggAAgTAgTACATCTCAC CCAgCAAAggATgCAggggT SEQ. ID NO: 17 |

The sequences (5'-3') of two aptamers of type A (light chain) and one aptamer of type B (light chain) for BoTox are shown. The complementary strand of one aptamer for BoTox (type A-light chain) was also sequenced.

Figure 14:
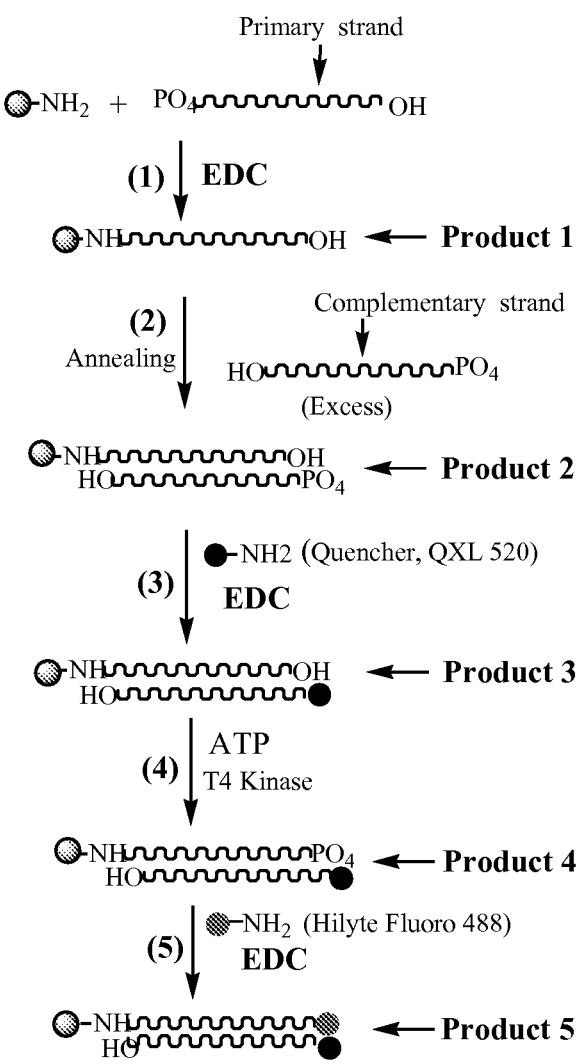
FIG. 14 represents a schematic of an exemplary preparation of aptamer/fluorephore/quencher complexes.

Preparation of Aptamer/Fluorephore/Quenching Agent Complexes is Demonstrated in One exemplary method displayed in FIG. 14. Two of the BoTox aptamers were selected by rapid selection processes disclosed herein (LCA (light chain A) and LCB) and the other two aptamers were selected using a state of the art method, SELEX (LCA and LCB).

Preparation of an exemplary DCE System. In one example experiment, a DCE system has a primary strand aptamer with a fluorophore (or quantum dot) covalently linked to the 3' side and a bead covalently linked to the 5'side. The complementary strand aptamer has a quencher covalently linked to the 5'side. The two strands of DNA are annealed together and the quencher decreases the fluorescence of the fluorophore (quantum dot) and in some embodiments, the quenching agent quenches the fluorophore. When a target agent is introduced to the DCE system the double strands denature, enabling them to fluoresce brightly. The procedures are shown in FIG. 15.

FIG. 14 is a schematic representation of preparation procedures of DNA Capture Element System. Hilyte Fluor 488 and QXL 520 were used as fluorophore and quencher respectively.

Certain advantages of methods disclosed herein are an improvement over the SELEX process. In some embodiments, rapid selection processes have some advantages over currently practiced methods. For example, aptamers selected by a rapid selection process disclosed herein can possess better specificity or selectivity (only a couple of aptamers are selected, not a couple of dozen aptamers like SELEX); it is much faster (selection process only needs 2 hours) than SELEX (selection process needs several months) and selection processes disclosed herein are very simple and low cost as compared to SELEX.

Primary DNA aptamer is added to amino polybeads (108 nm) in 0.1 M MOPS buffer. EDC and imidazole are then added. (Average # of primary strand DNA/bead=5.5) The reaction mixture is stirred at room temperature overnight. Product 1 is separated by centrifuge and washed with H2O, then re-suspended in MOPS buffer.

Excess complementary DNA is added to product 1 in 0.1M MOPS buffer. The mixture is stirred (or shaken) for one day at 60° C. and then for several days at room temperature. Product 2 is separated by centrifuge and washed with $H_2O$.

Product 2 is added to a saturated solution of QXL 520 with EDC and imidazole (excess quencher is used). This reaction mixture is stirred overnight. Product 3 is separated by centrifuge and washed with $H_2O$.

Product 3 is re-suspended in 10 ml of reaction buffer (350 ul 2M Tri-HCl, 100 ul of 1M $MgCl_2$, and 7.7 mg of DTT+ $H_2O$). Then 5 ml of ATP (27.6 mg ATP+H2O) and 2 ul of T4 Polynucleotide Kinase are added. The reaction mixture is shaken for 1-2 hr at 37° C. Product 4 is separated by centrifuge and washed with $H_2O$.

Product 4 is added to a solution of Hilyte Fluor 488 with EDC and imidazole in MOPS buffer (excess Hilyte Fluor 488 is used). The mixture is stirred overnight. Product 5 is separated by centrifuge and washed with $H_2O$ and re-suspended in 1×PBS buffer (with $Ca^{2+}$ and $Mg^{2+}$)

Four DCE systems made from aptamers of BoTox are selected to study the specificity of each aptamer. Two of them were selected against BoTox (type A & B; light chain) by rapid selection processes, and other two were selected against BoTox (type A and Holotoxin) by SELEX. Table 6 shows the sequences of the four aptamers and their complementary strands.

In one exemplary method interactions of BoTox agents (Type A and B, light and heavy chain) with aptamer/fluorophore/quencher complexes is studied. In one exemplary illustration, FIG. 15 demonstrates interaction of aptamer/fluorophore/quencher complexes with BoTox agents.

TABLE 6

Sequences of four aptamers and their complementary strands used to make DNA Aptamers Selected by a rapid selection process against BoTox, type A-light chain (for DCE-1)

1(+). AgTCTAgAgggCCCCAgAATACACCCgACAACTAgATACCCATC AAAAgTCCAgCAAAggATgCAgggT SEQ. ID NO: 18

1(-). ACCCCTgCATCCTTTgCTggACTTTTgATgggTATCTAgTTgTC gggTgTATTCTggggCCCTCTAgACT, SEQ. ID NO: 19

Selected by a rapid selection process against BoTox, type B-light chain (for DCE-2)

2(+). AgTCTAgAgggCCCCAgAATTATCCACTAgCgggAAgTAgTACA TCTCACCCAgCAAAggATgCAgggT, SEQ. ID NO: 20

2(-). ACCCCTgCATCCTTTgCTgggTgAgATgTACTACTTCCCgCTAg TggATAATTCTggggCCCTCTAgACT, SEQ. ID NO: 21

Selected by SELEX against BoTox, type a-light chain (for DCE-3)

3(+). CATCCgTCACACCTgCTCTggggATgTgTggTgTTggCTCCCgT ATCAAgggCgAATTCT, SEQ. ID NO: 22

3(-). gTAggCAgTgTggACgAgACCCCTACACACCACAACCgAgggCA TAgTTCCCgCTTAAgA, SEQ. ID NO: 23

Selected by SELEX against BoTox Holotoxin (for DCE-4)

4(+). CATCCgTCACACCTgCTCTgCTATCACATgCCTgCTgAAgTggT gTTggCTCCCgTATCA, SEQ. ID NO: 24

4(-). gTAggCAgTgTggACgAgACgATAgTgTACggACgACTTCACCA CAACCgAgggCATAgT, SEQ. ID NO: 25

Fluorescent change resulting from interaction of aptamer/fluorophore/quencher complexes. FIGS. 16-19 demonstrates fluorescent change resulting from interactions of BoTox agents (type A&B, light & heavy chain) with four BoTox aptamer complexes (two aptamers selected by a rapid selection process, and two selected by SELEX) The abbreviations on the diagrams represent the following (LCA: Light chain-type A; LCB: light chain-type B; Botox Holotoxin: Holotoxin means the light chain linked to the heavy chain by disulfide bonds to give the whole toxin). FIG. 16. represents fluorescent change resulting from interactions of BoTox aptamer (selected against type A-light chain, using a rapid selection process) with BoTox toxins. FIG. 17 represents fluorescent change resulting from interactions of BoTox aptamer (selected against type B-light chain, using a rapid selection process) with Botox toxins. FIG. 18 represents fluorescent change resulting from interactions of BoTox aptamer (selected against type A-light chain, SELEX process) with BoTox toxins. FIG. 19 represents fluorescent change resulting from interactions of BoTox aptamer (selected against BoTox Holotoxin, SELEX Process) with Botox toxin.

In one exemplary method, FIGS. 16-19 were compared for aptamer/fluorophore/quencher (reporter molecule) complexes dequenching results. FIG. 16 represents that the aptamer/fluorophore/quencher complex (LCA aptamer using a rapid selection process) is strongly denatured by BoTox light chain-type A. It is weakly denatured by BoTox light chain-type B. The complex is not denatured by BoTox heavy chain-type A&B. FIG. 17 represents that the aptamer/fluorophore/quencher complex (LCB aptamer using a rapid selection process) is only denatured by BoTox light chain-type B and relatively little is denatured by BoTox heavy chain-type A&B, and light chain-type A. FIG. 18 represents that the aptamer/fluorophore/quencher complex (LCA aptamer by SELEX process) is denatured by all four BoTox agents (light and heavy chain, type A and B). FIG. 19 represents that the aptamer/fluorophore/quencher complex (Holotoxin by SELEX process) is denatured by all four Botox agents (light and heavy chain, type A and B).

Results of FIGS. 16-19 that aptamers selected by methods disclosed herein (e.g. a rapid selection process) possess better specificity or selectivity than those selected by other processes like the SELEX process.

In one exemplary method, a simulation field test with Bt spores against Bt aptamer quench system is represented (see for example, FIG. 20). In this exemplary embodiment, Q-dots in the Bt aptamer quench system can be replaced by organic dye (Hilyte Fluor. 488). The quenching in this particular example is QXL 520. The Bt spores (*Bacillus thuringiensis* is also known at Bt) were derived from flies which stop in Bt spores contaminated area. The flies were washed and the supernatant was collected as the testing samples. Sample 1 is positive control, samples 2, 3, and 4 are different concentration of Bt spores. In this exemplary method, Bt aptamers were selected by a rapid selection process disclosed herein. FIG. 20 illustrates a fluorescent change after adding Bt spores to Bt aptamer system (125 sensitivity). FIG. 20 represents 50 μl of Bt aptamer (+30 ul PBS) were used (Bt aptamer made by rapid selection process) and 20 μl Bt spores were used for each sample.

In another exemplary method, shows the fluorescent change after adding Bt spores to Bt aptamer system (120 sensitivity). Pictures 1-4 show quenched and dequenched Bt DCE at visible and 530 nm (fluorescence) wavelengths. One exemplary difference between FIGS. 20 and 21 is that the results were tested at different instrument sensitivities but each example used the same aptamer, same amount of Bt spores, same time etc. except the sensitivity. In this example, organic dye (Hilyte Flour. 488) and quencher (QXL 520) were used in Bt DCE system. In one ePicture 1: Bt DCE before introduction of Bt spores at range of visible light (made on Nov. 21, 2007, Bt aptamer made by ASExp process)

In one exemplary method, Bt DCE were analyzed before introduction of Bt spores at 530 nm light (fluorescence, data not shown). In certain examples, a degree of fluorescence is evident if the fluorophores are not quenched completely. Additional experimental procedures can include introduction of Bt DCE after introduction of Bt spores at range of visible light. The data represented after dequenching illustrates strong fluorescence by associating the BT DCE with BT spores.

Some Exemplary Biological Agent Taggants
Methods

Exemplary aptamer labeling: Methods for making aptamers/DNA capture element contemplated have been described herein. In one example, *Bacillus thuringiensis* v. *kurstaki*, or *Bacillus anthracis* (Sterne), were coated and noncovalently linked to DALM by production in *E. coli* strain JM109/pIC2ORNR1.1 (American Type Culture Collection #69905) in which the respective DCE was inserted. Spores were treated with rare earth oxides with and without the intervening presence of the aptamers DALM. Spores from *Bacillus thuringiensis* (BT) and *Bacillus anthracis* (BA) were grown and harvested in accordance with standard procedures. The BA used was non-pathogenic Sterne strain used in veterinary vaccines (Thraxol; produced by Mobay Corporation, Animal Health Division, Shawnee, Kans. 66201). Solutions (0.1% w/v) of europium oxide and neodymium oxide (Aldrich) were prepared in double distilled water (ddH2O). One organic semiconductor diazoluminomelanin (DALM) was biosynthesized by *E. coli*. To dope the *bacillus* spores, 1.2× 10$^8$ spores were added to 200 μL of biosynthesized DALM in 1.5 mL microfuge tubes and incubated overnight (ON) at 4° C. Supernatant was removed and the spores were washed 2 times with ddH20. 200 μL of 0.1% lanthanide metal (europium oxide; neodymium oxide) was added to the tubes, which were then mixed ON at 4° C. Spores were again centrifuged and washed 2 times with ddH2O, Spores were resuspended in 70% EtOH. Spores were then pipetted onto filters (e.g. Whatman Nylon Membrane filters), which were in turn air-dried. Controls were missing various components in the coating solutions.

An Ocean Optics LIBS system consisting of a laser (Big Sky Ultra Nd:YAG 50 mJ laser), sampling chamber and LIBS2000+ spectrometer was used for the correlation results. The probe consisted of a bundle of seven 600-micron optical fibers arranged just above the site of plasma formation (5 to 10 mm) at a 45-degree angle to acquire plasma emission. Optical fibers in the probe carried the emission acquired from the plasma to the spectrometer. The majority of the analyses were carried out with the multichannel high-resolution LIBS spectrometer (200 to 980 nm wavelength range with approximately 0.1 nm spectral resolution FWHM). To assess the discrimination capabilities with a lower resolution broadband LIBS spectrometer, a single-channel LIBS system (200 to 1100 nm with approximately 1 nm spectral resolution FWHM) was also used.

Exemplary sample preparation for laser induced breakdown spectroscopy. Twenty-five single-shot spectra were acquired at different spots on the nylon filters to assess the discriminating capabilities of LIBS using the mid-resolution LIBS spectrometer. A 2-microsecond Q-switch setting was used to delay data acquisition for 2 microseconds after the laser event to allow the plasma continuum to decay. A correlation library was built by saving the average of 6 or 10 spectra acquired at different spots on the nylon filter into the correlation library. A large body of the accumulated data was subjected to linear and rank correlation analysis using for example the OOILIBS software.

LIBS elemental analysis. In one example, strong separation of spore types by the presence of metals (endogenous and exogenous). In this example, *Bacillus thuringiensis* spores were mixed with scandium oxide in the original preparation, which was missing in the anthrax spores. Europium was present in both spore preparations, but coating with europium was more pronounced on the *Bacillus thuringiensis* spores. In one experiment, the ability to distinguish rare earth labels (europium and neodymium) emission lines were analyzed (data not shown). *Bacillus thuringiensis* spore spectra were observed. All of the observed europium and neodymium emission lines appear between 350 and 550 nm. Correlation of LIBS of samples of *Bacillus anthracis* and *Bacillus thuringiensis* spores with various coatings such as europium oxide; anthrax spores coated with DCEs 6 and 8 and europium; *Bacillus thuringiensis* (BT) spores coated with DCEs 6 and 8 and europium; BT spores coated with DALM; BT spores coated with DALM and europium; spores coated with DALM, DCEs, and europium were all analyzed. LIBS spectra of *Bacillus thuringiensis* spores coated with rare earths have been demonstrated. The bacterial insecticide, *Bacillus thuringiensis*, were successfully coated with DNA capture elements, diazoluminomelanin, and rare earth metal ions.

All of the COMPOSITIONS and/or METHODS and/or APPARATUS disclosed and claimed herein can be made and executed without undue experimentation in light of the present disclosure. While the compositions and methods have been described in terms of preferred embodiments, it will be apparent to those of skill in the art that variation may be applied to the COMPOSITIONS and/or METHODS and/or APPARATUS and in the steps or in the sequence of steps of the method described herein without departing from the concept, spirit and scope of herein. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept as defined by the appended claims.

What is claimed is:

1. A composition comprising at least one double-stranded nucleic acid molecule, the at least one double-stranded nucleic acid molecule comprising:
   a reporter moiety bound to a fully-annealed first strand of the double-stranded nucleic acid molecule wherein the reporter moiety is capable of generating a signal; and
   a signal reducing moiety bound to a second, separate and fully complementary strand of the first nucleic acid strand wherein the signal reducing moiety is capable of reducing the signal produced by the reporter moiety,
   wherein the first and the second strand of the double-stranded nucleic acid molecule are the same length, and wherein either the first nucleic acid strand or the second nucleic acid strand of the double-stranded nucleic acid molecule is an aptamer and binds in a non-complementary manner to a target agent.

2. The composition of claim 1, further comprising a solid substrate, wherein the solid substrate is attached to either the first strand or the second strand of the double-stranded nucleic acid molecule.

3. The composition of claim 2, wherein the solid substrate is bound to the first strand.

4. The composition of claim 2, wherein the solid substrate comprises beads, microbeads, particles, microparticles, nanoparticles or a combination of two or more thereof.

5. The composition of claim 2, wherein the solid substrate is chosen from carboxy-terminated beads, hydrazine terminated beads, Silica beads, IDA (iminodiacetic acid) modified beads, aldehyde modified beads, Epoxy activated beads, DADPA- modified beads, biodegradable polymeric beads, microspheres with surface primary amine groups, amino-polystyrene particles, carboxyl-polystyrene particles, Epoxy-polystyrene particles, streptavidin coated beads, dimethylamino-polystyrene particles, hydroxy-polystyrene particles, colored particles, flow cytometry particles, sulfonate-polystyrene particles and a combination of two or more thereof.

6. The composition of claim 1, wherein the reporter moiety and the signal reducing moiety are a distance of 200 base pairs or less from one another.

7. The composition of claim 1, wherein the double-stranded nucleic acid molecule ranges from 10 to 200 base pairs in length.

8. The composition of claim 1, wherein the target agent is chosen from a virus, a yeast, a spore, a bacterium, a biomarker for disease, a biomarker for disease progression or a combination thereof.

9. The composition of claim 1, wherein the target agent comprises a non-nucleic acid target agent and the non-nucleic acid target is selected from the group consisting of, a whole organism comprising bacteria, yeast or virus; protein, peptide, carbohydrate, polysaccharide, glycoprotein, lipid, hormone, receptor, antigen, allergen, antibody, substrate, metabolite, cofactor, enzyme, metal ion, inhibitor, drug, pharmaceutical, nutrient, toxin, poison, explosive, pesticide, chemical warfare agent, biohazardous agent, prion, radioisotope, vitamin, heterocyclic aromatic compound, carcinogen, mutagen, narcotic, amphetamine, barbiturate, hallucinogen, waste product, or a contaminant.

10. The composition of claim 1, wherein the target agent is a protein.

11. The composition of claim 1, wherein at least one strand of the double-stranded nucleic acid molecule interacts with the target agent by secondary structure features.

12. The composition of claim 1, wherein the reporter moiety is a quantum dot.

13. A composition comprising, a quenching agent moiety bound to at least one separate and fully complementary strand of a fully-annealed dsDNA molecule, wherein absorption wavelength of the quenching agent moiety overlaps with emission wavelength of an agent capable of generating a signal, wherein one of the separate and fully complementary strands of the fully-annealed dsDNA molecule is an aptamer and binds in a non-complementary manner to a non-nucleic acid target agent, and wherein the strands of the dsDNA molecule are the same length.

14. The composition of claim 13, wherein the agent capable of generating a signal is a quantum dot.

15. A method for producing the at least one double-stranded nucleic acid molecule of claim 1, the method comprising:
   a) contacting a first reagent moiety with a first nucleic acid molecule mixture to form a first reagent moiety-nucleic acid molecule complex comprising nucleic acid molecules attached to first reagent moieties; and
   b) contacting a second reagent moiety with a second nucleic acid molecule mixture to form a second reagent moiety-nucleic acid molecule complex comprising nucleic acid molecules attached to second reagent moieties;
   wherein the first reagent moiety comprises a reporter moiety that is capable of generating a signal or a signal reducing moiety that is capable of reducing the signal from the reporter moiety and the second reagent moiety comprises the other of a reporter moiety or a signal reducing moiety;
   wherein either of the first nucleic acid molecule mixture or the second nucleic acid molecule mixture comprises at least one aptamer, and wherein the other of the first nucleic acid molecule mixture or second nucleic acid molecule mixture comprises a nucleic acid molecule fully complementary to and equal in length to the at least one aptamer; and
   c) combining the first nucleic acid molecule mixture and the second nucleic acid molecule mixture under conditions such that the at least one aptamer fully anneals to the complementary nucleic acid molecule.

16. The method of claim 15, wherein the first reagent moiety, second reagent moiety or combination thereof are in solution.

17. The method of claim 15, further comprising attaching a solid substrate to the strand bound to the reporter moiety.

* * * * *